US009296991B2

(12) United States Patent
Geerligs et al.

(10) Patent No.: US 9,296,991 B2
(45) Date of Patent: Mar. 29, 2016

(54) INFECTIOUS BRONCHITIS VACCINES DERIVED FROM IB-QX-LIKE VACCINE STRAINS

(75) Inventors: Harmen Jacob Geerligs, AR Weesp (NL); Cindy Aleida Maria Meinders, JJ Almere (NL); Geert Jan Boelm, AG Ede (NL); Bastiana Geertruida Elisabeth Stuurman, DJ Woerden (NL)

(73) Assignee: Zoetis Services LLC, Florham Park, NJ (US)

( * ) Notice: Subject to any disclaimer, the term of this patent is extended or adjusted under 35 U.S.C. 154(b) by 627 days.

(21) Appl. No.: 13/057,876

(22) PCT Filed: Aug. 7, 2009

(86) PCT No.: PCT/US2009/053085
§ 371 (c)(1),
(2), (4) Date: May 20, 2011

(87) PCT Pub. No.: WO2010/017440
PCT Pub. Date: Feb. 11, 2010

(65) Prior Publication Data
US 2011/0305726 A1  Dec. 15, 2011

Related U.S. Application Data

(60) Provisional application No. 61/087,228, filed on Aug. 8, 2008.

(51) Int. Cl.
*A61K 39/215* (2006.01)
*A61K 39/12* (2006.01)
*C12N 7/00* (2006.01)
*C12N 1/36* (2006.01)
*A61K 39/00* (2006.01)

(52) U.S. Cl.
CPC . *C12N 7/00* (2013.01); *A61K 39/12* (2013.01); *A61K 39/215* (2013.01); *A61K 2039/5254* (2013.01); *A61K 2039/541* (2013.01); *A61K 2039/544* (2013.01); *A61K 2039/552* (2013.01); *A61K 2039/70* (2013.01); *C12N 2770/20034* (2013.01); *C12N 2770/20064* (2013.01)

(58) Field of Classification Search
None
See application file for complete search history.

(56) References Cited

U.S. PATENT DOCUMENTS

| 7,208,164 B2 | 4/2007 | Jongsma et al. |
| 2008/0026449 A1 | 1/2008 | Melson et al. |

FOREIGN PATENT DOCUMENTS

| EP | 0639640 | * 10/2000 |
| WO | WO2004/078203 | * 9/2004 |

OTHER PUBLICATIONS

GenBank DQ431199 (IBV isolate L-1148 S-glycoprotein sequence)—identical to SEQ ID No. 2 of instant application.*
Bijlenga et al., 2004. Development and use of the H strain of avian infectious bronchitis virus from the Netherlands as a vaccine: a review. Avian Pathology (Dec. 2004) 33 (6), 550-557.*
Worthington, et al. A reverse transcriptase-polymerase chain reaction survey of infectious bronchitis virus genotypes in Western Europe from 2002 to 2006. Avian Pathol. 2008; 37(3): 247-257.*
Tarpey, et al. Safety and efficacy of an infectious bronchitis virus used for chicken embryo vaccination. Vaccine, 2006; 24: 6830-6838.*
Adzhar et al. "Universal Oligonucleotides for the Detection of Infectious Bronchitis Virus by the Polymerase Chain Reaction" Avian Pathology vol. 25 No. 4 (1996) pp. 817-836.
Altschul et al. "Basic Local Alignment Search Tool" Journal of Molecular Biology vol. 215 Issue 3 (1990) pp. 403-410.
Casais "Recombinant Avian Infectious Bronchitis Virus Expressing a Heterologous Spike Gene Demonstrates that the Spike Protein is a Determinant of Cell Tropism" Journal of Virology vol. 77 No. 16 Aug. 2003 pp. 9084-9089.
Casais et al. "Reverse Genetics System for the Avian Coronavirus Infectious Bronchitis Virus" Journal of Virology vol. 75 No. 24 Dec. 2001 pp. 12359-12369.
Chomcznski and Sacchi "Single-step Method of RNA Isolation by Acid Guanidinium Thiocyanate-phenol-chloroform Extraction" Analytical Biochemistry vol. 162 (1987) pp. 156-159 (submitted as abstract).
Domanska-Blicharz et al. "New Variant of IBV in Poland" Veterinary Record vol. 158 Jun. 10, 2006 p. 808.
Gough et al. "Chinese QX Strain of Infectious Bronchitis Virus Isolated in the UK" Veterinary Record vol. 162 Jan. 19, 2008 pp. 99-100.
Hodgson et al. "Recombinant Infectious Bronchitis Coronavirus Beaudette with the Spike Protein Gene of the Pathogenic M41 Strain Remains Attenuated but Induces Protective Immunity" Journal of Virology vol. 75 No. 24 Dec. 2004 pp. 13804-13811.
Huang et al. "Development of Attenuated Vaccines from Taiwanese Infectious Bronchitis Virus Strains" Vaccine vol. 24 (2006) pp. 785-791.
Huang et al. "Sequence Changes of Infectious Bronchitis Virus Isolates in the 3'7.3 kb of the Genome After Attenuating Passage in Embryonated Eggs" Avian Pathology vol. 36 No. 1 Feb. 2007 pp. 59-67.
Jones et al. "Efficacy of Live Infectious Bronchitis Vaccines Against a Novel European Genotype, Italy 02" The Veterinary Record vol. 156 No. 20 May 14, 2005 pp. 646-647.

(Continued)

*Primary Examiner* — Daniel E Kolker
*Assistant Examiner* — Stuart W Snyder
(74) *Attorney, Agent, or Firm* — Kelly M. Sullivan

(57) ABSTRACT

The present invention relates to infectious bronchitis (IB) viruses derived from a recently identified genotype of IB virus known as IB-QX, or from viruses that are genetically related to IB-QX, herein referred to as IB-QX-like viruses. The IB viruses of the invention may be live and attenuated or inactivated. Live, attenuated IB viruses of the invention may be produced by serial passaging of an IB-QX-like virus. The IB viruses of the invention are useful for, inter alia, vaccines against IB-QX and IB-QX-like viruses. Heretofore, known vaccine strains of IB viruses have proven insufficient to protect against infectious bronchitis caused by IB-QX and IB-QX-like viruses.

4 Claims, No Drawings

(56) References Cited

OTHER PUBLICATIONS

Li Jing et al. "Detection of Turkey Rhinotracheitis Virus in Turkeys Using the Polymerase Chain Reaction" Avian Pathology vol. 22 No. 4 (1993) pp. 771-783.

Liu et al. "S1 Gene Sequence Heterogeneity of a Pathogenic Infectious Bronchitis Virus Strain and its Embryo-passaged, Attenuated Derivatives" Avian Pathology vol. 36 No. 3 Jun. 2007 pp. 231-234.

Liu et al. "Genetic Delivery of Avian Infectious Bronchitis Coronavirus Strains Isolated in China Between 1995 and 2004" Archives of Virology vol. 151 (2006) pp. 1133-1148.

Pan et al. "Avian Infectious Bronchitis Virus S1 Spike Protein (S1) Gene, Partial Cds" GenBank AF193423.1.

Terregino et al. "Pathogenicity of a QX Strain of Infectious Bronchitis Virus in Specific Pathogen Free and Commericial Broiler Chickens, and Evaluation of Protection Induced by a Vaccination Programme Based on the Ma5 and 4/91 Serotypes" Avian Pathology vol. 37 No. 5 Oct. 2008 pp. 487-493.

Worthington et al. "A Reverse Transcriptase-polymerase Chain Reaction Survey of Infectious Bronchitis Virus Genotypes in Western Europe from 2002 to 2006" Avian Pathology vol. 37 No. 3 Jun. 2008 pp. 247-257.

Liu, S. et al., 2004, A new genotype of nephropathogenic infectious bronchitis virus circulating in vaccinated and non-vaccinated flocks in China., Avian Pathology 33(3), 321-327.

* cited by examiner

SEQUENCE LISTING

<160> NUMBER OF SEQ ID NOS: 8

<210> SEQ ID NO 1
<211> LENGTH: 1657
<212> TYPE: DNA
<213> ORGANISM: Infectious Bronchitis Virus QX

<400> SEQUENCE: 1

```
atgttgggga agtcactgtt tttagtgacc attttgtgtg cactatgtag tgcaaatttg      60
ttcgattctg ctaataatta tgtgtactac taccaaagtg cctttaggcc tccaaatgga     120
tggcatttgc aaggggggtgc ttatgcagta gtgaattcca ctaattatag taataatgca     180
ggttctgcac ctcagtgcac tgttggtgtt attaaggacg tctataatca aagtgcggct     240
tctatagcta tgacagcacc tcttcagggt atggcttggt ctaagtcaca attttgtagt     300
gcacactgta acttttctga aattacagtt tttgtcacac attgttatag tagtggtagc     360
gggtcttgtc ctataacagg catgattcca cgtgatcata ttcgtatttc tgcaatgaaa     420
```

-continued

```
aatggttctt tatttttataa tttaacagtt agcgtatcta aatacccctaa ttttaaatct    480
tttcaatgtg ttaacaactt cacatctgtt tatttaaatg gtgatcttgt ttttacttcc    540
aacaaaacta ctgatgttac gtcagcaggt gtgtattta aagcaggtgg acctgtaaat     600
tataatatta tgaaagaatt taaggttctt gcttactttg ttaatggtac agcacaagat    660
gtaattttgt gcgataattc ccccaagggt ttgctagcct gtcaatataa cactggcaat    720
ttttcagatg gctttatcc ttttactaat agtactttag ttagggaaaa gttcattgtc     780
tatcgcgaaa gtagtgttaa tactactctg gcgttaacta atttcacttt tactaatgta    840
agtaatgcac agcctaatag tggtggtgtt aatactttc atttatatca aacacaaaca     900
gctcagagtg gttattataa ttttaatttg tcatttctga gtcagtttgt gtataaggca    960
agtgatttta tgtatgggtc ttaccaccct agttgttctt ttagaccaga aaccattaat   1020
agtggtttgt ggtttaattc cttgtcagtt tctcttactt atggacccct acagggaggg   1080
tgtaagcaat ctgttttag tggtaaggca acgtgttgtt atgcctactc ttataatggc    1140
ccaagggcat gtaaaggtgt ttattcaggt gaattaagca tgaatttga atgtggattg    1200
ctggtttatg ttactaagag tcatggctct cgtatacaga ctagaacgga gcccttagta   1260
ttaacgcaac acaattataa taatattact ttagataagt gtgttgctta aatatatat    1320
ggcagagtag gccaaggttt tattactaat gtgactgatt ctgctgctaa ttttagttat   1380
ttagcagatg gtgggttagc tatttagat acgtcgggtg ccatagatgt ttttgttgta    1440
aagggcagct atggtcttaa ttattacaag gttaatcctt gtgaagatgt taaccaacag   1500
tttgtagtgt ctggtggcaa tatagttggc attcttactt ctagaaatga aacaggttct   1560
gaacaggttg agaaccagtt ttatgttaag ttaccaata gctcacatcg tcgcaggcgt    1620
tctattggcc aaaacgtaac aacttgccct tatgtta                            1657
```

<210> SEQ ID NO 2
<211> LENGTH: 601
<212> TYPE: PRT
<213> ORGANISM: Infectious Bronchitis Virus QX Like L1148

<400> SEQUENCE: 2

```
Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Gln
            20                  25                  30

Ser Ala Phe Arg Pro Pro Asn Gly Trp His Leu Gln Gly Gly Ala Tyr
        35                  40                  45

Ala Val Val Asn Ser Thr Asn Tyr Thr Asn Asn Ala Gly Ser Ala His
    50                  55                  60

Glu Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
        115                 120                 125

Ile Pro Arg Asp His Ile Arg Ile Ser Ala Met Lys Asn Gly Ser Leu
    130                 135                 140

Phe Tyr Asn Leu Thr Val Ser Val Ser Lys Tyr Pro Asn Phe Lys Ser
```

-continued

```
            145                 150                 155                 160
        Phe Gln Cys Val Asn Asn Phe Thr Ser Val Tyr Leu Asn Gly Asp Leu
                        165                 170                 175
        Val Phe Thr Ser Asn Lys Thr Thr Asp Val Thr Ser Ala Gly Val Tyr
                        180                 185                 190
        Phe Lys Ala Gly Gly Pro Val Asn Tyr Ser Ile Met Lys Glu Phe Lys
                        195                 200                 205
        Val Leu Ala Tyr Phe Val Asn Gly Thr Ala Gln Asp Val Val Leu Cys
                        210                 215                 220
        Asp Asn Ser Pro Lys Gly Leu Leu Ala Cys Gln Tyr Asn Thr Gly Asn
        225                 230                 235                 240
        Phe Ser Asp Gly Phe Tyr Pro Phe Thr Asn Ser Thr Leu Val Arg Glu
                        245                 250                 255
        Lys Phe Ile Val Tyr Arg Glu Ser Ser Val Asn Thr Thr Leu Ala Leu
                        260                 265                 270
        Thr Asn Phe Thr Phe Thr Asn Val Ser Asn Ala Gln Pro Asn Ser Gly
                        275                 280                 285
        Gly Val Asn Thr Phe His Leu Tyr Gln Thr Gln Thr Ala Gln Ser Gly
                        290                 295                 300
        Tyr Tyr Asn Phe Asn Leu Ser Phe Leu Ser Gln Phe Val Tyr Lys Ala
        305                 310                 315                 320
        Ser Asp Phe Met Tyr Gly Ser Tyr His Pro Ser Cys Ser Phe Arg Pro
                        325                 330                 335
        Glu Thr Ile Asn Ser Gly Leu Trp Phe Asn Ser Leu Ser Val Ser Leu
                        340                 345                 350
        Thr Tyr Gly Pro Leu Gln Gly Gly Cys Lys Gln Ser Val Phe Ser Gly
                        355                 360                 365
        Lys Ala Thr Cys Cys Tyr Ala Tyr Ser Tyr Lys Gly Pro Met Ala Cys
                        370                 375                 380
        Lys Gly Val Tyr Ser Gly Glu Leu Ser Thr Asn Phe Glu Cys Gly Leu
        385                 390                 395                 400
        Leu Val Tyr Val Thr Lys Ser Asp Gly Ser Arg Ile Gln Thr Arg Thr
                        405                 410                 415
        Glu Pro Leu Val Leu Thr Gln Tyr Asn Tyr Asn Asn Ile Thr Leu Asp
                        420                 425                 430
        Lys Cys Val Ala Tyr Asn Ile Tyr Gly Arg Val Gly Gln Gly Phe Ile
                        435                 440                 445
        Thr Asn Val Thr Asp Ser Ala Ala Asn Phe Ser Tyr Leu Ala Asp Gly
                        450                 455                 460
        Gly Leu Ala Ile Leu Asp Thr Ser Gly Ala Ile Asp Val Phe Val Val
        465                 470                 475                 480
        Gln Gly Ile Tyr Gly Leu Asn Tyr Tyr Lys Val Asn Pro Cys Glu Asp
                        485                 490                 495
        Val Asn Gln Gln Phe Val Val Ser Gly Gly Asn Ile Val Gly Ile Leu
                        500                 505                 510
        Thr Ser Arg Asn Glu Thr Gly Ser Glu Gln Val Glu Asn Gln Phe Tyr
                        515                 520                 525
        Val Lys Leu Thr Asn Ser Ser His Arg Arg Arg Arg Ser Ile Gly Gln
                        530                 535                 540
        Asn Val Thr Ser Cys Pro Tyr Val Ser Tyr Gly Arg Phe Cys Ile Glu
        545                 550                 555                 560
        Pro Asp Gly Ser Leu Lys Met Ile Val Pro Glu Glu Leu Lys Gln Phe
                        565                 570                 575
```

```
Val Ala Pro Leu Leu Asn Ile Thr Glu Ser Val Leu Ile Pro Asn Ser
            580                 585                 590

Phe Asn Leu Thr Val Pro Pro Arg Asn
        595                 600

<210> SEQ ID NO 3
<211> LENGTH: 567
<212> TYPE: PRT
<213> ORGANISM: Infectious Bronchitis Virus QX LIke L1449-2

<400> SEQUENCE: 3

Met Leu Val Lys Ser Leu Phe Val Thr Ile Leu Cys Ala Leu Cys
  1               5                  10                  15

Ser Ala Asn Leu Phe Asp Ser Asp Asn Tyr Val Tyr Tyr Tyr Gln
             20                  25                  30

Ser Ala Phe Arg Pro Pro Asn Gly Trp His Leu Gln Gly Gly Ala Tyr
             35                  40                  45

Ala Val Val Asn Ser Thr Asn Tyr Thr Asn Asn Ala Gly Ser Ala His
         50                  55                  60

Gly Cys Thr Val Gly Val Ile Lys Asp Val Tyr Asn Gln Ser Val Ala
 65                  70                  75                  80

Ser Ile Ala Met Thr Ala Pro Leu Gln Gly Met Ala Trp Ser Lys Ser
                 85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
            115                 120                 125

Ile Pro Arg Asp His Ile Arg Ile Ser Ala Met Lys Asn Gly Ser Leu
        130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Ile Leu Cys
    210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Thr Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
```

```
                     340                 345                 350
Thr Tyr Gly Pro Leu Gln Gly Gly Cys Lys Gln Ser Val Phe Ser Gly
                355                 360                 365

Lys Ala Thr Cys Cys Tyr Ala Tyr Ser Tyr Lys Gly Pro Met Ala Cys
            370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
        435                 440                 445

Thr Asn Val Thr Asp Ser Ala Ala Asn Phe Ser Tyr Leu Ala Asp Gly
            450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
        515                 520                 525

Val Lys Leu Thr Asn Ser Ser His Arg Arg Arg Arg Ser Ile Gly Gln
            530                 535                 540

Asn Val Thr Ser Cys Pro Tyr Val Ser Tyr Gly Arg Phe Cys Ile Glu
545                 550                 555                 560

Pro Asp Gly Ser Leu Lys Met
                565

<210> SEQ ID NO 4
<211> LENGTH: 582
<212> TYPE: PRT
<213> ORGANISM: Infectious Bronchitis Virus QX Like 1449-10

<400> SEQUENCE: 4

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Asn Ser Thr Asn Tyr Thr Asn Asn Ala Gly Ser Ala His
    50                  55                  60

Glu Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Gly Gly Ser Gly Ser Cys Pro Ile Thr Gly Met
        115                 120                 125

Ile Pro Arg Asp His Ile Arg Ile Ser Ala Met Lys Asn Gly Ser Leu
    130                 135                 140
```

-continued

```
Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Ile Leu Cys
    210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Thr Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
        355                 360                 365

Lys Ala Thr Cys Cys Tyr Ala Tyr Ser Tyr Lys Gly Pro Met Ala Cys
370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
        435                 440                 445

Thr Asn Val Thr Asp Ser Ala Ala Asn Phe Ser Tyr Leu Ala Asp Gly
    450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
        515                 520                 525

Val Lys Leu Thr Asn Ser Ser His Arg Arg Arg Ser Ile Gly Gln
    530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Glu Leu Lys Gln Phe
```

```
                565                 570                 575
Val Ala Pro Leu Leu Asn
            580

<210> SEQ ID NO 5
<211> LENGTH: 24
<212> TYPE: DNA
<213> ORGANISM: Infectious Bronchitis Virus primer

<400> SEQUENCE: 5
taatactggy aatttttcag atgg                                          24

<210> SEQ ID NO 6
<211> LENGTH: 22
<212> TYPE: DNA
<213> ORGANISM: Infectious Bronchitis Virus primer

<400> SEQUENCE: 6
aatacagatt gcttacacca cc                                            22

<210> SEQ ID NO 7
<211> LENGTH: 18
<212> TYPE: DNA
<213> ORGANISM: Infectious Bronchitis Virus primer

<400> SEQUENCE: 7
gcttatgcag tagtcaat                                                 18

<210> SEQ ID NO 8
<211> LENGTH: 22
<212> TYPE: DNA
<213> ORGANISM: Infectious Bronchitis Virus primer

<400> SEQUENCE: 8
cacgtggaat catgcctgtt at                                            22
```

INFECTIOUS BRONCHITIS VACCINES DERIVED FROM IB-QX-LIKE VACCINE STRAINS

CROSS-REFERENCE TO RELATED APPLICATIONS

This application is a national phase entry of international application number PCT/US2009/053085, filed Aug. 7, 2009, which claims priority from U.S. provisional application No. 61/087,228, filed Aug. 8, 2008. The disclosures of the above-identified provisional application and of the above-identified international application are herein incorporated by reference in their entireties.

FIELD

The present invention relates to the field of vaccines against avian infectious diseases. More specifically, the invention relates to novel vaccines against infectious bronchitis (IB) virus.

BACKGROUND

Infectious bronchitis (IB) virus is a coronavirus that causes respiratory disease in domestic fowl (e.g., chickens). IB disease symptoms include, e.g., respiratory distress, reduced weight, reduced egg production, increased frequency of abnormal eggs, and increased rates of mortality.

Several different genotypes and serotypes of IB viruses have been identified. Genotyping of IB viruses is generally accomplished by sequencing all or part of the gene that encodes the S1 (spike) protein of the virus. The S1 protein is the N-terminal cleavage product of a larger S glycoprotein encoded by the genome of IB viruses. The C-terminal cleavage product of the S glycoprotein is referred to as the S2 protein. The S1 protein is responsible for cell attachment and is a major antigenic determinant for IB viruses. Exemplary genotypes (or "strains") of IB virus include 793B, Massachusetts, Italy02, D274, Arkansas, B1648 and D1466. (See, e.g., Worthington et al. (June 2008), *Avian Pathology* 37:247-257).

A novel genotype of IB virus, designated "QX" (also referred to as "QXIBV"), was first identified in China in the late 1990s. (See Liu et al. (2006), *Archives of Virology* 151: 1133-1148). Since the identification of the original QX genotype, numerous IB virus genotypes with a high degree of similarity/identity to QX at the S1 nucleotide sequence level have been identified worldwide. These "IB-QX-like" viruses (as further defined herein) have been identified, e.g., in France, Germany, Netherlands, Belgium, United Kingdom, Italy and Poland.

Clearly, IB-QX-like viruses pose a serious threat to the poultry industry. Notwithstanding the rapidly emerging significance of this type of IB virus, heretofore, no vaccines specific for IB-QX-like viruses have been available or described in the art. Commercially available IB vaccines (live, attenuated strains) have been found to be ineffective in protecting chickens against IB-QX-like viruses. Thus, there exists a need in the art for new vaccine compositions and methods of vaccination that provide specific protection against IB-QX and IB-QX-like viruses.

BRIEF SUMMARY OF THE INVENTION

The present invention satisfies the aforementioned need in the art by providing IB viruses that are useful, inter alia, as antigenic components in vaccine compositions that protect against infection by IB-QX and IB-QX-like viruses. The invention includes live, attenuated versions of IB-QX-like viruses. Such live, attenuated strains can be produced, e.g., by serially passaging IB-QX-like viruses until adequate attenuation is obtained. The present invention also includes inactivated versions of IB-QX-like viruses. IB-QX-like viruses for use in the context of the present invention can be obtained, e.g., from deposited strains of IB-QX-like viruses, field cases of IB-QX-like virus infection, or by construction of recombinant IB viruses expressing defined, predetermined gene segments such as a particular S1 gene sequence.

The present invention also provides vaccine compositions comprising live, attenuated or killed strains of IB-QX-like viruses, as well as methods for making live, attenuated and/or killed strains of IB-QX-like viruses. The present invention also provides methods for vaccinating a bird against infectious bronchitis by administering to the bird a vaccine composition comprising live, attenuated or killed strains of IB-QX-like viruses. Other aspects of the present invention will be evident from the Detailed Description of the Invention and Examples set forth herein below.

BRIEF DESCRIPTION OF THE DRAWINGS

None.

DETAILED DESCRIPTION

The present invention provides isolated IB viruses derived from IB-QX-like viruses.

As used herein, the term "IB-QX-like virus" means any virus with an S1 protein encoded by a nucleotide sequence that is at least 95% identical to the nucleotide sequence that encodes the S1 protein of the original IB-QX strain. The nucleotide sequence that encodes the S1 protein of the original IB-QX strain is represented by SEQ ID NO:1 (See Table 1) and is available under NCBI Genbank Accession No. AF193423.

TABLE 1

Nucleotide Sequence of the S1 Gene of Strain IB-QX atgttggggaagtcactgttttttagtgaccattttgtgtgcactatgtag tgcaaatttgttcgattctgctaataattatgtgtactactaccaaagtg cctttaggcctccaaatggatggcatttgcaaggggtgcttatgcagta gtgaattccactaattatagtaataatgcaggttctgcacctcagtgcac tgttggtgttattaaggacgtctataatcaaagtgcggcttctatagcta tgacagcacctcttcagggtatggcttggtctaagtcacaattttgtagt gcacactgtaacttttctgaaattacagttttttgtcacacattgttatag tagtggtagcgggtcttgtcctataacaggcatgattccacgtgatcata ttcgtatttctgcaatgaaaaatggttctttattttataatttaacagtt agcgtatctaaataccctaatttaaatcttttcaatgtgttaacaactt cacatctgtttatttaaatggtgatcttgtttttacttccaacaaaacta ctgatgttacgtcagcaggtgtgtattttaaagcaggtggacctgtaaat tataatattatgaaagaatttaaggttcttgcttactttgttaatggtac agcacaagatgtaattttgtgcgataattcccccaagggtttgctagcct TABLE 1-continued Nucleotide Sequence of the S1 Gene of Strain IB-QX gtcaatataacactggcaattttcagatggcttttatccttttactaat agtactttagttagggaaaagttcattgtctatcgcgaaagtagtgttaa tactactctggcgttaactaatttcacttttactaatgtaagtaatgcac agcctaatagtggtggtgttaatacttttcatttatatcaaacacaaaca gctcagagtggttattataattttaatttgtcatttctgagtcagtttgt gtataaggcaagtgatttatgtatgggtcttaccaccctagttgttctt ttagaccagaaaccattaatagtggtttgtggtttaattccttgtcagtt tctcttacttatggacccctacagggagggtgtaagcaatctgttttttag tggtaaggcaacgtgttgttatgcctactcttataatggcccaagggcat gtaaaggtgtttattcaggtgaattaagcatgaattttgaatgtggattg ctggtttatgttactaagagtcatggctctcgtatacagactagaacgga gcccttagtattaacgcaacacaattataataatattactttagataagt gtgttgcttataatatatgcgagagtaggccaaggttttattactaat gtgactgattctgctgctaatttagttatttagcagatggtgggttagc tattttagatacgtcgggtgccatagatgtttttgttgtaaagggcagct atggtcttaattattacaaggttaatccttgtgaagatgttaaccaacag tttgtagtgtctggtggcaatatagttggcattcttacttctagaaatga aacaggttctgaacaggttgagaaccagttttatgttaagttaaccaata gctcacatcgtcgcaggcgttctattggccaaaacgtaacaacttgccct tatgtta (SEQ ID NO: 1)

Thus, any virus with an S1 protein encoded by a nucleotide sequence that is at least 95% identical to SEQ ID NO:1 is an "IB-QX-like" virus for purposes of the present invention. Examples of IB-QX-like viruses are set forth in Worthington et al. (June 2008), *Avian Pathology* 37:247-257, including the IB virus genotypes designated L-1148 (also referred to in Worthington et al. as "NL/L-1148/04"), 1449-2 (also referred to in Worthington et al. as "NL/L-1449K/04"), 1449-10 (also referred to in Worthington et al. as "NL/L-1449T/04"), and Roberton (also referred to in Worthington et al. as FR/L-1450T/05). Exemplary IB-QX-like strains from which the IB viruses of the present invention may be derived are set forth in Table 2, below. For purposes of the present invention, the term IB-QX-like virus includes, inter alia, the original QX IB virus.

TABLE 2

Exemplary IB-QX-like Viruses

| Virus Designation | NCBI Genbank Accession No. (S1 Gene) |
|---|---|
| NL/L-1148/04 (L-1148) | DQ431199 |
| NL/L-1449K/04 (1449-2) | EF079115 |
| NL/L-1449T/04 (1449-10) | EF079116 |
| FR/L-1450L/05 (Roberton) | EF079117 |
| FR/L-1450T/05 | EF079118 |
| K10217-03 | AY790363 |
| IS/1201 | DQ400359 |
| K1255-03 | AY790364 |
| K3-3 | AY790367 |
| CK/CH/LSD/031 | DQ167148 |

TABLE 2-continued

Exemplary IB-QX-like Viruses

| Virus Designation | NCBI Genbank Accession No. (S1 Gene) |
|---|---|
| CK/CH/LLN/981 | DQ167145 |
| QX | AF193423 |
| LS2 | AY278246 |
| A2 | AY043312 |
| HBN | DQ070837 |
| NMC | DQ973113 |
| IBVQ | DQ480155 |
| SH | DQ480156 |
| CK/CH/LXJ/021 | DQ167152 |
| LX4 | AY189157 |
| CK/CH/LSHH/031 | DQ 167149 |
| CK/CH/LJL/041 | DQ 167144 |
| CK/CH/LHLJ/04XI | DQ 167140 |
| CK/CH/LSHH/03II | DQ 167150 |
| CK/CH/LHLJ/04V | DQ 167139 |
| CK/CH/LHLJ/991 | DQ167142 |
| DB03 | AB274271 |
| LH2 | AY180958 |
| CK/CH/LHLJ/07V | EU563943 |
| CK/CH/LHLJ/07I | EU563942 |
| HH06 | EF577030 |
| WF | DQ480151 |

In addition to sequence comparison of S1 coding sequence, other methods can be used to identify IB-QX-like viruses. Such methods may be used, e.g., as preliminary screens for identifying candidate IB-QX-like viruses from a large pool of viral samples. If a virus tests positive for being IB-QX-like by one of these preliminary screens, the genotype of that virus can then be confirmed by S1 nucleotide gene sequencing and comparison as described elsewhere herein. An exemplary "preliminary" method for identifying IB-QX-like viruses (or putative IB-QX-like viruses) is serum neutralization in which antiserum from an animal infected with IB-QX or an IB-QX-like virus is tested for its ability to neutralize a candidate virus. Positive neutralization results may suggest that the candidate virus is an IB-QX-like virus.

Another exemplary, preliminary screening method for IB-QX-like viruses, is restriction fragment length polymorphism (RFLP). Here, a DNA copy of the S1 gene from a candidate virus is produced by RT-PCR. The DNA copy is then exposed to a restriction enzyme that is known to cut the S1 gene of IB-QX-like strains at positions that are not cut in the S1 gene of non-IB-QX-like strains (or vice versa). Differences in restriction fragment digestion can be visualized by size separation of the resulting digested DNA, e.g., by gel electrophoresis.

The isolated IB viruses of the present invention can be derived from any of the IB-QX-like viruses mentioned herein as well as from any other IB-QX-like viruses that can be isolated from the field. Additional IB-QX-like viruses may be obtained by methods known to persons of ordinary skill in the art. For example, IB-QX-like viruses may be obtained by screening samples (e.g., oropharyngeal swabs) taken from chickens suspected of being infected with IB virus or otherwise exhibiting one or more symptoms of infectious bronchitis. RNA is isolated from such samples and a DNA copy of the S1 gene or portion thereof is generated by reverse transcriptase-polymerase chain reaction (RT-PCR). The S1 DNA copy is then sequenced, and the nucleotide sequence thus obtained is compared against the nucleotide sequence of the S1 gene of IB QX (SEQ ID NO:1) and the percent identity between the two sequences is determined.

In certain exemplary embodiments, the present invention includes isolated IB viruses derived from an IB-QX-like virus having an S1 protein with the same amino acid sequence as the S1 protein of IB-QX-like viruses L-1148 (SEQ ID NO:2), 1449-2 (SEQ ID NO:3), or 1449-10 (SEQ ID NO:4). The amino acid sequences of the S1 proteins from these strains are shown in Table 3:

TABLE 3

Amino acid sequences of S1 proteins of exemplary IB-QX-like viruses.

| IB-QX-like Strain | Amino Acid Sequence of S1 Gene |
|---|---|
| L-1148 | MLVKSLFLVTILCALCSANLFDSDNNYVYYYQSAFRPPNGWHLQGG<br>AYAVVNSTNYTNNAGSAHECTVGVIKDVYNQSVASIAMTAPLQGMA<br>WSKSQFCSAHCNFSEITVFVTHCYSSGSGSCPITGMIPRDHIRISAM<br>KNGSLFYNLTVSVSKYPNFKSFQCVNNFTSVYLNGDLVFTSNKTTD<br>VTSAGVYFKAGGPVNYSIMKEFKVLAYFVNGTAQDVVLCDNSPKGL<br>LACQYNTGNFSDGFYPFTNSTLVREKFIVYRESSVNTTLALTNFTFT<br>NVSNAQPNSGGVNTFHLYQTQTAQSGYYNFNLSFLSQFVYKASDF<br>MYGSYHPSCSFRPETINSGLWFNSLSVSLTYGPLQGGCKQSVFSG<br>KATCCYAYSYKGPMACKGVYSGELSTNFECGLLVYVTKSDGSRIQT<br>RTEPLVLTQYNYNNITLDKCVAYNIYGRVGQGFITNVTDSAANFSYL<br>ADGGLAILDTSGAIDVFVVQGIYGLNYYKVNPCEDVNQQFVVSGGNI<br>VGILTSRNETGSEQVENQFYVKLTNSSHRRRSIGQNVTSCPYVSY<br>GRFCIEPDGSLKMIVPEELKQFVAPLLNITESVLIPNSFNLTVPPRN<br>(SEQ ID NO: 2) |
| 1449-2 | MLVKSLFLVTILCALCSANLFDSDNNYVYYYQSAFRPPNGWHLQGG<br>AYAVVNSTNYTNNAGSAHGCTVGVIKDVYNQSVASIAMTAPLQGM<br>AWSKSQFCSAHCNFSEITVFVTHCYSSGSGSCPITGMIPRDHIRISA<br>MKNGSLFYNLTVSVSKYPNFKSFQCVNNFTSVYLNGDLVFTSNKTT<br>DVTSAGVYFKAGGPVNYSIMKEFKVLAYFVNGTAQDVILCDNSPKG<br>LLACQYNTGNFSDGFYPFTNSTLVREKFIVYRESSVNTTLALTNFTF<br>TNVSNAQPNSGGVNTFHLYQTQTAQSGYYNFNLSFLSQFVYKASD<br>FMYGSYHPSCSFRPETINSGLWFNSLSVSLTYGPLQGGCKQSVFS<br>GKATCCYAYSYKGPMACKGVYSGELSTNFECGLLVYVTKSDGSRI<br>QTRTEPLVLTQYNYNNITLDKCVAYNIYGRVGQGFITNVTDSAANFS<br>YLADGGLAILDTSGAIDVFVVQGIYGLNYYKVNPCEDVNQQFVVSG<br>GNIVGILTSRNETGSEQVENQFYVKLTNSSHRRRSIGQNVTSCPY<br>VSYGRFCIEPDGSLKM (SEQ ID NO: 3) |
| 1449-10 | MLVKSLFLVTILCALCSANLFDSDNNYVYYYQSAFRPPNGWHLQGG<br>AYAVVNSTNYTNNAGSAHECTVGVIKDVYNQSVASIAMTAPLQGMA<br>WSKSQFCSAHCNFSEITVFVTHCYSGGSGSCPITGMIPRDHIRISAM<br>KNGSLFYNLTVSVSKYPNFKSFQCVNNFTSVYLNGDLVFTSNKTTD<br>VTSAGVYFKAGGPVNYSIMKEFKVLAYFVNGTAQDVILCDNSPKGL<br>LACQYNTGNFSDGFYPFTNSTLVREKFIVYRESSVNTTLALTNFTFT<br>NVSNAQPNSGGVNTFHLYQTQTAQSGYYNFNLSFLSQFVYKASDF<br>MYGSYHPSCSFRPETINSGLWFNSLSVSLTYGPLQGGCKQSVFSG<br>KATCCYAYSYKGPMACKGVYSGELSTNFECGLLVYVTKSDGSRIQT<br>RTEPLVLTQYNYNNITLDKCVAYNIYGRVGQGFITNVTDSAANFSYL<br>ADGGLAILDTSGAIDVFVVQGIYGLNYYKVNPCEDVNQQFWSGGNI<br>VGILTSRNETGSEQVENQFYVKLTNSSHRRRSIGQNVTSCPYVSY<br>GRFCIEPDGSLKMIVPEELKQFVAPLLN (SEQ ID NO: 4) |

The isolated IB viruses of the present invention can also be produced by persons of ordinary skill in the art using recombinant, or "reverse genetics" methods. For example, Casais et al. (2003) *J. Virol.* 77:9084-9089, describe the construction of a recombinant IB virus expressing a heterologous spike gene. (See also Hodgson et al. (2004) *J. Virol.* 78:13804-13811). This system involves the use of an IB virus infectious clone, i.e., a full length IB virus cDNA cloned into a vector such as, e.g., a vaccinia viral vector. (See, e.g., Casais et al. (2001) *J. Virol.* 75:12359-12369). Starting with an IB virus infectious clone, recombinant IB viruses expressing the S1 protein of any other IB virus can be constructed. Thus, using the system of Casais et al. or variations thereof, recombinant IB viruses can be easily made that express the S1 protein from any IB-QX-like virus (i.e., an S1 protein encoded by a polynucleotide sequence that is at least 95% identical to SEQ ID NO:1), thereby producing recombinant IB-QX-like viruses. Recombinant IB-QX-like viruses thus produced can be used in the context of the present invention in the same manner that naturally obtained IB-QX-like viruses (e.g., field isolates) are used, as described in detail herein.

As used herein, "percent identity" means that percentage of nucleotides in a reference nucleotide sequence identical to the nucleotides in the subject sequence (or specified portion thereof) after aligning the sequences and introducing gaps, if necessary, to achieve the maximum percent sequence identity as generated by the program WU-BLAST-2.0a19 (Altschul et al. (1997) *J. Mol. Biol.* 215:403-410; hereinafter referred to as "BLAST") with all of the search parameters set to default values. A percent nucleotide sequence identity value is determined by the number of matching identical nucleotides divided by the sequence length for which the percent identity is being reported.

Although IB-QX-like viruses are known in the art, IB viruses that are derived from IB-QX-like viruses have not been described or suggested in the art and are thus the subject of the present invention. As used herein, the term "derived from," in relation to an IB virus, means that the IB virus is either: (1) a serially passaged descendent of an IB-QX-like virus; or (2) an IB-QX-like virus that has been subjected to conditions that inactivate the virus or render it less virulent. A virus "derived from" an IB-QX-like virus may therefore be either live/attenuated or inactivated/killed.

As noted above, an IB virus derived from IB-QX-like virus, in certain embodiments, is a serially passaged descendent of an IB-QX-like virus. A "serially passaged descendent of an IB-QX-like virus" is defined herein as a virus that is obtained after an IB-QX-like virus is propagated in an environment conducive to virus replication, removed from said environment, and then propagated at least one additional time in the same or similar environment. Each cycle of propagation and removal is considered a single "passage." A serially passaged descendent of an IB-QX-like virus is preferably attenuated; e.g., the attenuation is the result of serial passaging.

An exemplary method of serially passaging IB viruses (including IB-QX-like viruses) involves the use of embryonated domestic fowl (e.g., chicken) eggs as the environment conducive to virus replication. For instance, embryonated chicken eggs are inoculated with a quantity of IB-QX-like virus via the allantoic cavity. The inoculated eggs are incubated at, e.g., 37° C. for 24 hours (or under other suitable incubation conditions, times and temperatures). The allantoic fluid is harvested from the eggs. At this point, the virus has been passaged "1×." The harvested allantoic fluid from the first passage, at appropriate dilution, is then inoculated into new embryonated eggs, which are incubated at, e.g., 37° C. for 24 hours, and the allantoic fluid is harvested from this second set of eggs. At this point, the virus has been passaged "2×." Continued passaging in this manner can continue indefinitely. Alternative environments conducive to virus replication that can be used to passage IB viruses include, e.g., cell cultures such as chicken kidney cell cultures or chicken embryonic fibroblast cultures.

Although incubation at 37° C. for 24 hours is mentioned herein as an exemplary incubation step for passaging IB viruses, a person of ordinary skill in the art will understand that other temperatures and/or times of incubation may be used. For example, embryonated eggs may be incubated at temperatures ranging from 20° C. to 42° C. The time of incubation for virus passaging can range from 4 hours to 4 days, and more preferably from 16 to 36 hours.

Samples of virus can be tested after each passage (or after every $2^{nd}$, $4^{th}$, $5^{th}$, $10^{th}$, etc. passage) for degree of virulence. Degree of virulence can be determined by, e.g., administering the passaged virus to chicks and assessing various parameters indicative of infectious bronchitis. Exemplary parameters include: (i) ciliary activity of tracheal explants; (ii) clinical signs such as, e.g., watery exudates from eye or nose, gasping, or diarrhea; (iii) gross pathological examination of, e.g., upper airways, kidneys, spleen and/or intestine; and (iv) histology of the trachea, lung and kidney. Exemplary measurements of each of these parameters are presented in Example 2, below. An IB virus derived from an IB-QX-like virus by serial passaging is deemed "attenuated" if one or more of the parameters indicative of infectious bronchitis is reduced, eliminated, or improved relative to the corresponding parameters observed in chicks that are infected with the parental (non-passaged) IB-QX-like virus. Comparison may also be made to chicks infected with other known virulent strains of IB virus.

A non-limiting, exemplary method for assessing virulence of a serially passaged IB virus derived from an IB-QX-like virus is illustrated in Example 2. Briefly, chicks that have been inoculated with a serially passaged IB virus derived from an IB-QX-like virus are given a numerical score reflecting (i) ciliary activity of tracheal explants, (ii) clinical signs, and (iii) pathological examination. The total score [(i)+(ii)+(iii)] is determined. Virulence classifications are established as follows:

"Not Virulent," if the total score is less than or equal to the total score of a non-challenged control group;

"Mild," if the total score is greater than the total score of a non-challenged control group but less than or equal to the total score for a group challenged with a known mild strain of IB virus (e.g., POULVAC IB H120 (Massachusetts strain), Fort Dodge Animal Health, Fort Dodge, Iowa).

"Moderate Virulent," if the total score is higher than the total score for a group challenged with a known mild strain of IB virus but less than or equal to the total score for a group challenged with a known virulent strain of IB virus (e.g., the parental IB-QX-like strain or other known virulent strain such as strain IB-M41).

"Virulent," if the total score is equal to or higher than the total score for a group challenged with a known virulent strain of IB virus.

An IB virus that is classified as "Not Virulent" or "Mild" in accordance with the foregoing classification scheme is suitable as a live attenuated vaccine strain. In certain circumstances, a "Moderate Virulent" IB virus may also be useful as a live attenuated strain.

Alternative methods for assessing the suitability of a serially passaged IB-QX-like virus as a vaccine strain are known in the art and are illustrated elsewhere herein, e.g., in Example 3. As shown in Example 3, cilia scores and kidney and trachea morphology are used to determine the degree of attenuation following multiple passages. These parameters can in turn be used to determine whether a given strain is suitable (e.g., sufficiently safe) for vaccine purposes.

As noted above, the other category of IB virus that is "derived from" an IB-QX-like virus is an IB-QX-like virus that has been subjected to conditions that inactivate the virus or render it less virulent. In contrast to serially passaged IB viruses, which are typically live and attenuated, IB viruses within this second category are typically regarded as inactivated or killed. Methods of inactivating viruses, including IB viruses, are known in the art.

Thus, as the above discussion illustrates, an IB virus of the present invention which is derived from an IB-QX-like virus may be inactivated or attenuated. If inactivated, the IB viruses of the present invention may be inactivated by contacting the viruses with an inactivating compound such as, e.g., β-propiolactone or formalin. If attenuated, the IB viruses of the present invention may be attenuated by serial passaging, starting with an initial passage of an IB-QX-like virus. The IB viruses may be passaged in any environment conducive to viral replication. Such environments include, e.g., embryonated domestic fowl eggs. Embryonated domestic fowl eggs include, e.g., embryonated chicken eggs such as specific pathogen free (SPF) chicken eggs. Other suitable environments include, e.g., cell cultures.

To attenuate the IB viruses of the present invention, the viruses may be passaged any number of times. In certain embodiments, the viruses are passaged at least enough times so that the resulting viruses are characterized as being either "Not Virulent," "Mild," or (in certain circumstances) "Mild Virulent," using the classification methodology referred to elsewhere herein. In certain exemplary embodiments, the IB viruses of the present invention are passaged between 5 and 400 times. For example, the IB viruses may be passaged 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400 times, or more if necessary or desired.

The IB viruses of the present invention are preferably isolated. As used herein, the term "isolated" means that the viruses are not contained within a tissue of a live animal.

The present invention includes several non-limiting working examples of isolated infectious bronchitis viruses derived from IB-QX-like viruses. For example, IB-QX-like virus L-1148 was passaged 64 times in 10-11 day embryonated specific pathogen free (SPF) chicken eggs. For the 65$^{th}$ passage, SPF eggs were inoculated with 0.2 mL of a 1000-fold dilution of the allantoic fluid from passage level 64. After 24 hours of incubation at 37° C., the allantoic fluid was harvested in pools. The 65$^{th}$ passaged material is referred to herein as L-1148(p65) (see Example 3). Sterile pools of L-1148(p65) were selected, pooled, mixed with a stabilizer, filled in 3 mL vials (1 mL per vial) and lyophilized to make master seed virus IB QX L1148 MSV65. An additional 15 passages were carried out, for a total of 80 passages, to produce L-1148(p80) (see Example 3). As with the 65$^{th}$ passaged material, the allantoic fluid from the 80$^{th}$ passage was harvested in pools. Sterile pools were selected, pooled, mixed with a stabilizer, filled in 3 mL vials (1 mL per vial) and lyophilized to make master seed virus IB QX L1148A MSV80. IB QX L1148 MSV65 and IB QX L1148A MSV80 were each passaged an additional five times to yield IB QX L1148A MSV65 X+5 and IB QX L1148A MSV80 X+5, respectively.

IB QX L1148 MSV65 was deposited with the European Collection of Cell Cultures, Porton Down, UK (ECACC) on Jun. 10, 2009, in the name of Fort Dodge Animal Health, and was assigned provisional accession No. 09061002.

IB QX L1148A MSV80 was deposited with the European Collection of Cell Cultures, Porton Down, UK (ECACC) on Jun. 10, 2009, in the name of Fort Dodge Animal Health, and was assigned provisional accession No. 09061004.

IB QX L1148A MSV65 x+5 was deposited with the European Collection of Cell Cultures, Porton Down, UK (ECACC) on Jun. 10, 2009, in the name of Fort Dodge Animal Health, and was assigned provisional accession No. 09061003.

IB QX L1148A MSV80 x+5 was deposited with the European Collection of Cell Cultures, Porton Down, UK (ECACC) on Jun. 10, 2009, in the name of Fort Dodge Animal Health, and was assigned provisional accession No. 09061001.

Additional non-limiting examples of IB viruses derived from IB-QX-like viruses are described elsewhere herein.

The present invention includes vaccine compositions comprising: (i) an isolated IB virus derived from an IB-QX-like virus; and (ii) a pharmaceutically acceptable carrier. The pharmaceutically acceptable carrier can be, e.g., water, a stabilizer, a preservative, culture medium, or a buffer, or any combination of the foregoing. Vaccine compositions of the invention can be prepared in the form of a suspension or in a lyophilized form or, alternatively, in a frozen form. If frozen, glycerol or other similar agents may be added to enhance stability when frozen.

The vaccine compositions of the present invention may comprise an adjuvant, particularly if the IB virus contained within the composition is inactivated (i.e., killed). The adjuvant can be an acrylic polymer, dimethyl dioctadecyl ammonium bromide (DDA), or a combination of an acrylic polymer and DDA. An acrylic polymer, as used herein, is any polymer or copolymer that contains an acrylic moiety. Exemplary acrylic polymers include, e.g., polyacrylic acid, methacrylic acid, methacrylate, acrylamide, acrylate, acrylnitrile, and alkyl-esters of poly acrylic acid. Examples of acrylic copolymers include, e.g., poly (acrylamide-co butyl, methacrylate), acrylic-methacrylic acid, acrylic-acrylamide and poly (methacrylate). Examples of commercially available acrylic polymers include, Carbopol (B. F. Goodrich Co., Cleveland, Ohio), Carboset, (B. F. Goodrich Co., Cleveland, Ohio), Neocryl (Avecia, Inc., Wilmington, Del.), and Eudragit (Rohm Tech, Inc., Malden, Mass.). A particularly preferred acrylic polymer for use in the emulsions of the present invention is Carbopol, which is also referred to as a water-soluble polymer of acrylic acid crosslinked with polyallyl sucrose. The adjuvant may be a water soluble or water dispersible adjuvant. The adjuvant may be an oil emulsion, e.g., water-in-oil, oil-in-water, or water-in-oil-in-water emulsion. A water-in-oil emulsion can further include one or more oil soluble surfactants, one or more water soluble surfactants, additional adjuvants, additional aqueous phase components, emulsion stabilizers, or combinations thereof.

The vaccine compositions of the present invention may comprise, in addition to an IB virus derived from an IB-QX-like virus, other antigenic components. The other antigenic components included in the vaccine compositions may be derived from infectious agents, e.g., infectious agents of chickens. For example, the vaccine compositions of the present invention may further comprise at least one additional live attenuated IB virus derived from a non-IB-QX-like virus. As used herein, "non-IB-QX-like virus" means any IB virus with an S1 protein encoded by a nucleotide sequence that is less than 95% identical to the nucleotide sequence that encodes the S1 protein of the original IB-QX strain. The nucleotide sequence that encodes the S1 protein of the original IB-QX strain is represented by SEQ ID NO:1 and is available under NCBI Genbank Accession No. AF193423. Thus, any virus with an S1 protein encoded by a nucleotide sequence that is less than 95% identical to SEQ ID NO:1 is a "non-IB-QX-like" virus for purposes of the present invention. Exemplary non-IB-QX-like viruses include strains such as Massachusetts, Arkansas, Georgia-98, Italy-02, 793-B, D274, D1466, or strains having the S1 genotype of any of the foregoing non-IB-QX-like viruses. Vaccine compositions of the present invention may contain one or more commercially available IB vaccine strains in addition to an IB virus derived from an IB-QX-like virus.

In certain embodiments of the present invention, the vaccine composition may contain an additional antigenic component derived from an infectious agent that is not an IB virus. For example, the vaccine compositions of the present invention may further comprise a live attenuated or inactivated avian virus such as Newcastle Disease virus, Marek's Disease virus, Infectious Bursal Disease virus, Reovirus, Avian Influenza virus, Chicken Anemia virus, or Avian Encephalomyelitis virus.

The present invention also includes methods for preparing live attenuated IB viruses. The live attenuated viruses prepared according to this aspect of the invention are useful for, inter alia, vaccinating chickens against IB virus. The methods according to this aspect of the invention comprise passaging an IB-QX-like virus. For example, an IB-QX-like virus can be passaged in embryonated fowl eggs (e.g., embryonated chicken eggs), or in cell culture (e.g., chicken kidney cell cultures). The number of times an IB-QX-like virus must be passaged in order to render it attenuated can be determined based on the teachings set forth herein. For example, after passaging an IB-QX-like virus, the resulting IB virus can be administered to chickens, and the chickens are then assessed for, e.g., ciliary activity of tracheal explants, clinical signs, gross pathology and/or histological signs of infectious bronchitis. A passaged IB virus that produces reduced or less severe indications of IB as compared to the parental IB-QX-like virus from which it was derived (or as compared to other known reference IB strains) is considered an attenuated strain, for purposes of the present invention. According to certain embodiments, the methods of the invention comprise passaging an IB-QX-like virus until the resulting virus is categorized as "Not Virulent" or "Mild" in accordance with the categorization methodology set forth elsewhere herein.

The present invention also includes methods for vaccinating a bird against infectious bronchitis. The methods according to this aspect of the invention comprise administering to the bird an IB virus derived from an IB-QX-like virus. The methods according to this aspect of the invention may comprise administering any vaccine composition comprising any IB virus derived from an IB-QX-like virus as described elsewhere herein. The vaccine compositions of the present invention may be administered in any manner such that the active or antigenic components are immediately or eventually brought into contact with the bird's respiratory mucosal membranes. Thus, the vaccine composition may be administered to birds, e.g., intranasally, orally, and/or intraocularly. The vaccine compositions for avian administration may be formulated as described above and/or in a form suitable for administration by spray, including aerosol (for intranasal administration) or in drinking water (for oral administration). The vaccine compositions of the present invention may also be administered subcutaneously, intramuscularly or in ovo. (See U.S. Pat. No. 7,208,164). According to this aspect of the invention, the vaccine compositions comprising an IB virus derived from an IB-QX-like virus may be administered to a bird at an age of 1 day to 18 weeks. If administered in ovo, the vaccine composition can be administered, e.g., in the last half of the incubation term. For example, in the case of chickens, eggs are generally inoculated from about incubation day 12 to about incubation day 20. Preferably, the inoculation occurs from between day 14 to about day 19. More preferably, the chicken eggs are inoculated at about day 15-18.

The following examples are illustrative, but not limiting, of the method and compositions of the present invention. Other suitable modifications and adaptations of the variety of conditions and parameters normally encountered in molecular biology and chemistry which are obvious to those skilled in the art in view of the present disclosure are within the spirit and scope of the invention.

EXAMPLES

Example 1

Identification of IB-QX-Like Viruses

This example provides a method for determining if a candidate IB virus is an IB-QX-like virus. Candidate IB viruses can be obtained from a variety of sources including, e.g., tissue swabs obtained from animals showing one or more symptoms of infectious bronchitis, or from a public depository.

As used herein, an "IB-QX-like virus" is an infectious bronchitis virus with an S1 nucleotide sequence that is at least 95% identical to the S1 nucleotide sequence of the originally-identified IB-QX strain. The S1 nucleotide sequence of the original IB-QX strain is SEQ ID NO:1, and can be found under NCBI Genbank Accession No. AF193423.

To ascertain whether a candidate virus is an IB-QX-like virus, RNA is isolated from a sample containing the candidate viral particles (e.g., tissue swabs) using standard RNA isolation methods. For example, RNA can be extracted using the guanidinium isothyocyanate, phenol-chloroform method. (Chomcznski and Sacchi (1987), *Analytical Biochemistry* 162:156-159; Li et al. (1993), *Avian Pathology* 22:771-783). In addition, several RNA isolation kits are commercially available and are suitable for this purpose. The RNA is then used in a reverse transcription-polymerase chain reaction (RT-PCR) to generate an amplified DNA copy of the full S1 gene or the so-called "hypervariable region" of the S1 gene. The primers used in the RT-PCR are preferably ones that are common for most known strains of IB virus. Exemplary primers, along with corresponding RT-PCR methods that can be used to amplify the hypervariable region of the S1 gene of candidate IB viruses are set forth in, e.g., Worthington et al. (June 2008), *Avian Pathology* 37:247-257, and Jones et al. (2005), *Veterinary Record* 156:646-647. In Worthington et al., a nested PCR is performed following the RT reaction to produce a DNA copy of the S1 hypervariable region having about 393 base pairs. Full length S1 sequencing can be performed using the method of Adzhar et al. (1996), *Avian Pathology* 25:817-836. Alternative primers and RT-PCR conditions suitable for amplifying the S1 gene or portions thereof can be easily designed by persons of ordinary skill in the art using publicly available sequence information for IB viruses.

After the nucleotide sequence of the entire S1 gene, or portion thereof (e.g., the hypervariable region), of the candidate IB virus is determined, this sequence is compared against the S1 gene sequence for strain IB-QX (SEQ ID NO:1) to determine percent identity. If the nucleotide sequence of the S1 gene, or hypervariable region thereof, of the candidate IB virus is at least 95% identical to the nucleotide sequence of the S1 gene of IB-QX (SEQ ID NO:1), then the candidate IB virus is considered an IB-QX-like virus.

Exemplary methods for determining whether a candidate IB virus is an IB-QX-like virus are also described, e.g., in Gough et al. (2008), *Veterinary Record* 162:99-100, and Domanska-Blicharz et al. (2006), *Veterinary Record* 158:808, both of which are incorporated by reference herein in their entireties.

Example 2

Attenuation of IB-QX-Like Viruses

Introduction

This example summarizes experiments in which IB-QX-like viruses were passaged multiple times in embryonated chicken eggs and attenuation of the resulting viruses was demonstrated in chickens.

Materials and Methods

Infectious Bronchitis Viruses

Three strains of IB-QX-like viruses, designated L-1148, 1449-2, and 1449-10, were used in this example. All three of these strains were identified as being IB-QX-like by S1 gene sequencing and nucleotide comparison to IB-QX and other IB-QX-like viruses. (See Worthington et al. (June 2008), *Avian Pathology* 37:247-257).

Strain L-1148 and strain 1449-10 were each passaged 50 times in embryonated chicken eggs; Strain 1449-2 was passaged 5 times in embryonated chicken eggs. The strains obtained from these multiple passages were designated L-1148(p50), 1449-10(p50), and 1449-2(p5), respectively. Thus, L-1148(p50) was derived from L-1148; 1449-10(p50) was derived from 1449-10; and 1449-2(p5) was derived from 1449-2.

Study Design

Chicks were challenged with L-1148(p50), 1449-10(p50), and 1449-2(p5) viruses, along with known mild (IB-H120, vaccine strain) and virulent (IB-M41) IB strains. An unchallenged control group was also included in the study. The study design is summarized in Table 4:

TABLE 4

Study Design.

| Group | No. of Chicks | Challenge Strain |
|---|---|---|
| 1 | 10 | L-1148(p50) |
| 2 | 10 | 1449-10(p50) |
| 3 | 10 | 1449-2(p5) |
| 4 | 10 | IB-H120 |
| 5 | 10 | IB-M41 |
| control | 10 | not challenged |

Animals and Husbandry Sixty SPF-chicks were used in this example. At 15 days of age, 50 chicks were divided in five groups (1-5) and housed in isolators. The 10 chicks that were used as controls stayed in their pen. In order to acclimatize, the chicks that were moved to isolators were left alone for three days. Food and water was available ad lib. All chicks were observed for clinical signs of IB throughout the study.
Administration of Viruses
Using a 1 ml syringe, 5 chicks in a row were challenged with IB virus by administering 0.1 ml to each eye of every chick. In the case of IB-M41 the chicks received 0.25 ml per eye. All chicks were challenged with approximately $10^{6.0}$ $EID_{50}$ IB virus at an age of 18 days. Virus stocks were stored at $-70°$ C. and diluted in nutrient broth to the appropriate concentration prior to administration.

Immediately after administering the viruses to the chicks, a sample of the used virus was stored in a sterile bottle at $-70°$ C. for re-titration.
Ciliary Activity of Tracheal Explants
Four days after the challenge, the ciliary activity of tracheal explants was examined. Chicks were stunned with a gas mixture of 34% $O_2$ and 66% $CO_2$. When a state of complete anesthesia was reached, the chicks were killed by inhaling 100% $CO_2$. Immediately after death the trachea (from the base of the head to 0.5 cm proximal from the syrinx) was removed. Immediately after the trachea was removed it was rinsed with PBS at 37° C. using a syringe without needle and stored in PBS of 37° C. until further processing. Transverse sections of 0.6 mm of the trachea were made using a McIlwain Tissue Chopper (Mickle Laboratory Engineering Co. Ltd., Surrey, United Kingdom). The transverse sections of the trachea were put with 2 ml PBS of 37° C. in a Petri-disc and were examined under the microscope within 4 minutes. Ciliary activity of 3 sections of the upper part, 4 sections of the middle part and 3 sections of the lower part of the trachea were examined by low-magnification (400×) microscopy. The ciliary activity of each tracheal section was examined within 20 minutes after killing the bird.

The ciliary activity was scored on a scale from 0 (100 percent ciliary activity) to 4 (0 percent ciliary activity). For each group the average ciliostasis was then calculated by dividing the sum of the tracheal sections that showed cessation by the number of chicks per group. The calculated average ciliostasis per group were compared to the average ciliostasis of the groups that were challenged with Poulvac IB 120 and IB-M41 and with the non-vaccinated group. IB-M41 is classified as virulent and the IB virus in Poulvac IB H120 as mild.
Clinical Signs
The birds were observed daily for clinical signs by animal technicians throughout the study. Clinical signs attributed to IB infection were scored as follows:

| Observable Clinical Sign | Score Absent | Score Present |
|---|---|---|
| Watery exudates from eye or nose | 0 | 2 |
| Gasping | 0 | 4 |
| Diarrhea | 0 | 1 |

Gross Pathological Examination
Necropsy was performed on each chick to determine any abnormality that could be a result of the IB infection. The deviations were scored as follows:
Upper airway: normal aspect=0; mucus=1; bronchitis/tracheitis=2.
Kidneys: normal aspect=0; swollen or pale, with urate crystals=1.
Spleen: normal aspect=0; swollen=1.
Intestine: normal aspect=0; abnormalities=2.
Histology of the Trachea, Lung and Kidney
Samples of trachea, lung and kidney were taken 4 days after administration of the viruses. All samples were subjected to histological examination. Immunohistochemical staining on IBV epitope 48.4 (a nucleoprotein) was applied to all samples in order to detect IBV.
Evaluation
The virulence of the IB viruses in SPF chicks was determined by:
The ciliary activity of tracheal explants;
The presence and seriousness of clinical signs; and
Abnormalities found at pathological examination.
The virulence of the IBV in SPF chicks was classified as:
Not virulent, if the total score of the group is less than or equal to the total score of the non-challenged group;
Mild, if the total score of the group is higher than the total score of the control group and less than or equal to the total score of the group challenged with Poulvac IB H120;
Moderate virulent, if the total score of the group is higher than the total score of the group challenged with Poulvac IB H120 and less than or equal to the total score of the group challenged with IB M4;
Virulent, if the total score of the group is equal or higher than the total score of the group challenged with IB-M41.

The test was not deemed valid if more than 10 percent of the chicks died from causes not attributable to the vaccine virus. In this Example, the vaccine virus was deemed sufficiently safe if:
No chicken showed notable clinical signs of avian infectious bronchitis or died from causes attributable to the vaccine virus;
The average ciliostasis score was not more than 25; and
At most moderate inflammatory lesions were seen during kidney histological examination.
Viruses that were classified as moderate virulent or virulent and which do not comply with the above mentioned requirements are nonetheless potentially suitable for use as a challenge virus.
Results
Titration of the IB Viruses after Administration to Chicks
The titers of the different IB viruses after challenging the chicks is presented in Table 5. As shown in this table, chicks were challenged with IB virus exceeding $10^{6.0}$ $EID_{50}$ in all cases.

TABLE 5

Titers of IBV after administration to chicks.

| Group | Virus | Sample 1 | Sample 2 | Average |
|---|---|---|---|---|
| | | Titer in 10log EID50 per ml or per vial | | |
| 1 | L-1148(p50) | 6.83 | 6.67 | 6.75 |
| 2 | 1449-10(p50) | 7.00 | 6.33 | 6.67 |
| 3 | 1449-2(p5) | 6.50 | 6.67 | 6.59 |
| 4 | IB-H120 | 6.33 | 6.00 | 6.17 |
| 5 | IB-M41 | 6.50 | 7.33 | 6.92 |

Clinical Signs, Ciliary Activity, and Pathologic Examination

No chicks died during the study. Only very mild oculonasal exsudative discharge (small droplets in the opening of the nose) and gasping after handling the chicks was observed in some chicks challenged with IB 1449-10(p50).

Ciliostasis was not observed in any of the control chicks, but was clearly demonstrated in the chicks challenged with IB-M41. Three out of 10 chicks challenged with Poulvac IB H120 virus showed complete ciliostasis. The number of tracheal sections with ciliostasis increased if chicks were challenged with IBV 1148(p50) (6 sections), IBV 1449-2(p5) (20 sections) and IBV 1449-10(p50) (41 sections).

During pathological examination of the chicks, it was found that in the chicks challenged with IB 1449-2(p5), Poulvac IB H120 or IB-M41 a catarrhal exsudate was present in the tracheas. In one chick, challenged with IB 1449-2(p5), a swollen pale kidney was found.

Based on ciliary activity, clinical signs and post mortem findings, summarized in Table 6, a classification of the IB-QX-like-derived viruses was made. Strain L-1148(p50) was classified as mild, IBV 1449-10(p50) as moderate virulent, and IBV 1449-2(p5) as slight virulent compared with Poulvac IB H120 and IB-M41.

TABLE 6

Classification of IB viruses after challenging SPF chicks.

| Group | Virus | Avg. Ciliostasis Score | C (n) | S | P | Total (C + S + P) | Classification |
|---|---|---|---|---|---|---|---|
| | | | Score* | | | | |
| 1 | L-1148(p50) | 2 | 24 (1) | 0 | 0 | 24 | Mild |
| 2 | 1449-10(p50) | 16 | 164 (4) | 24 | 0 | 188 | Moderate virulent |
| 3 | 1449-2(p5) | 8 | 80 (2) | 0 | 5 | 85 | Mild |
| 4 | IB-H120 | 12 | 120 (3) | 0 | 1 | 121 | Mild |
| 5 | IB-M41 | 40 | 400 (10) | 0 | 4 | 404 | Virulent |
| 6 | no challenge | 0 | 0 (0) | 0 | 0 | 0 | Not Virulent |

*Scores were based on:
(C) the ciliary activity of tracheal explants,
(n) = number of affected chicks; a chick is considered affected when at least two tracheal sections show ciliostasis.
(S) Clinical signs.
(P) Pathological examination.

Histology of the Trachea, Lungs and Kidney

No abnormalities were found in the tracheas of the chicks challenged with L-1148(p50), 1449-2(p5) and IB-H120. After challenging with 1449-10(p50) local tracheitis with necrosis was found in one out of four tracheas. All the tracheas of the chicks challenged with IB-M41 showed acute tracheitis. IBV could only be detected in the tracheas of chicks infected with IB-M41.

No abnormalities were found and no IBV was detected in the lungs of any of the chicks.

Histology of the kidneys of the chicks challenged with L-1148(p50) and 1449-10(p50) demonstrated slight infiltration of mononuclear and plasmacellular cells in some cases. The tubular epithelia was not affected. Using immunohistochemistry no IBV-antigen was detected in the epithelial cells of the tubula of the kidney samples taken 4 days after infection. No IBV could be detected in the kidneys of any groups after immunohistochemical coloring.

Discussion

IBV first infects the tracheal mucosa and then replicates in epithelia of other organs, e.g., the tubular epithelial cells of the kidneys and the epithelia of the oviduct. The replication of IBV in epithelial cells might result in degeneration of the cells and subsequently pathological changes in organs/tissues may occur. Whether clinical signs occur depends on several factors such as the virulence of the IBV, the organ infected, the occurrence of secondary infection and the overall fitness of the chick. This is seen in the trachea of the chicks challenged with IBV, where ciliary activity is impaired in all (IBV-M41), 40% (1449-10(p50)), 20% (1449-2(p5)) and 10% (IBV L-1148(p50)) of the animals. Catarrhal exsudate was present in the tracheas of chicks challenged with IBV 1449-2(p5), Poulvac IB H120 and IB-M41. Only when chicks were challenged with IBV 1449-10(p50) were mild clinical signs seen, which appears to have been the result of ciliostasis and subsequently the build-up of mucus. Bearing in mind that the chicks were challenged with high doses of IBV, the results of this Example are promising. The absence of clinical signs after challenging chicks with IBV L-1148(p50) and IBV 1449-2(p5) most likely reflects the fact that the clinical signs caused by the corresponding field strains are mild. Only mild respiratory signs were seen after challenging SPF chicks with IBV 1449-10(p50), which demonstrates the attenuation of this strain, because the field strain of IBV 1449-10 was virulent.

Conclusion

As shown in this example, IB-QX-like viruses can be attenuated by multiple passaging. The resulting attenuated strains derived from IB-QX-like viruses show great promise as new vaccine strains against infectious bronchitis. Passaged viruses derived from IB-QX-like viruses which cause moderate virulent effects when administered to chickens would be useful as challenge material in order to study and further develop novel IB vaccines, especially vaccines against IB-QX-like viruses.

Example 3

Further Passaging and Safety of IB-QX-Like Strain L-1148

Introduction

In this Example, IB-QX-like virus strain L-1148 was passaged multiple times in embryonated chicken eggs. The safety of the viruses at various passage levels was assessed by measuring the degree of ciliostasis and kidney morphology in chickens. As illustrated below, multiple passaging of strain L-1148 resulted in an attenuated strain suitable as a vaccine against infections by IB-QX-like viruses.

Passaging of L-1148 in Embryonated SPF Chicken Eggs

For virus passaging, 10 to 11 day embryonated specific pathogen free (SPF) chicken eggs were used. Strain L-1148 was initially passaged seven times in SPF chicken eggs. For the first 5 passages nondiluted allantoic fluid was inoculated. The passages were made only with allantoic fluids from eggs with live embryos. This resulted in approximately 50% dead embryos. It was decided to continue passaging with 100-fold diluted allantoic fluids in physiological salt solution, resulting in fewer dead embryos. Passages were continued until passage 73. Upon harvesting of passage 73 it became known that there was a contamination with Newcastle disease (ND) virus in the IB L-1148 strain. Blood samples from chickens vaccinated with passage 50 of strain IB L-1148 contained antibodies against an ND virus. RT-PCR analysis of samples of passage 8 revealed that strain IB L-1148 had been contaminated from the beginning with this virus. It was decided to stop passaging and to clean virus strain IB L-1148 from the contamination.

Decontamination of L-1148 Passages

Samples were taken from passages 22, 47 and 73 and were treated with ND specific antiserum. Briefly, samples of allantoic fluid were mixed with samples of ND specific polyclonal antiserum in an allantoic fluid : serum volume ratio of 1:2. The mixture was incubated at 37° C. for one hour followed by overnight incubation at 4° C. After incubation 10-fold dilution series were prepared and 5 eggs per dilution were inoculated each with 0.1 ml. After 2 days allantoic fluids were harvested and samples from the highest dilution that still were positive for IB by RT-PCR were collected. Eggs with dead embryos were discarded. The allantoic fluid again was treated with the ND antiserum as above and again a dilution series was inoculated in eggs. After incubation, again the highest dilution that still was positive for IB by RT-PCR was collected, filled in portions and frozen and stored at −70° C.

The foregoing decontamination process resulted in cleaned and cloned passages 24, 49 and 75. A batch at passage level 25 was made by inoculation of a $10^7$-fold dilution in eggs, 0.2 ml per egg, and harvesting after 48 hours incubation at 37° C. The allantoic fluid was filled in small portions and stored at −70° C. A batch of passage 50 was made according to the same procedure. Passage 75 was passaged further until passage 80. The allantoic fluids of passage 80 were pooled, filled in small portions and frozen and stored at −70° C.

Safety Testing

The safety of different passage levels of strain IB L-1148 in chickens was tested several times. Also included in the study was un-attenuated IB-QX-like strain 1449-10, along with virulent Massachusetts-like strain IB-M41 and mild vaccine strain Poulvac IB H120.

One-day old SPF chickens were used for each test. The tests were performed in accordance with standard procedures. Briefly, using a 1 ml syringe, 5 chicks in a row were challenged with IB virus by administering 0.1 ml to each eye of every chick. In the case of IB-M41 the chicks received 0.25 ml per eye. Freeze-dried virus was reconstituted in water for injections and further dilutions were prepared in nutrient broth. Subsequently, the birds were observed daily for clinical signs.

Five days after administration of virus, the ciliary activity of tracheal explants was examined for 5 chickens. The tracheas were removed from the euthanized chickens and transverse sections of 0.6 mm of the trachea were made, 3 sections of the upper part, 4 sections of the middle part and 3 sections of the lower part of the trachea. The transverse sections of the trachea were put in a Petri-disc containing 2 ml PBS of 37° C., and were examined under the microscope within 4 minutes.

The ciliary activity was scored microscopically, on a scale from 0 (100 percent ciliary activity) to 4 (0 percent ciliary activity). For each group the average ciliastasis was calculated by dividing the sum of the tracheal sections that show cessation by the number of chicks per group.

Samples of trachea, lung and kidney were taken from euthanized animals. All samples were examined histologically. Immunohistochemical staining for IBV epitope 48,4 (a nucleoprotein) was carried out in order to detect IB virus.

The results are summarized in Table 7.

TABLE 7

Summarized Results of Safety Tests on Different Passages of L-1148

| Study | Virus Tested | Titer* | Cilia Score | Kidneys | Trachea |
|---|---|---|---|---|---|
| A | 1449-10 | 5.6 | 39 | pale, swollen, severe nephritis | normal |
|  | 1449-10 | 3.0 | 32 | pale, swollen, severe nephritis | normal |
|  | IB H120 | 6.0 | 18 | mild nephritis | normal |
|  | L-1148(p8) | 6.0 | 39 | pale, swollen, mild to moderate nephritis | normal |
|  | L-1148(p25) | 6.0 | 18 | pale, swollen, mild to moderate nephritis | normal |
|  | L-1148(p40) | 6.0 | 21 | pale, swollen, mild nephritis | normal |
|  | L-1148(p50) | 6.0 | 31 | pale, swollen, mild nephritis | normal |
|  | IB-M41 | 3.3 | 37 | none | normal |
| B | IB-M41 | 3.3 | 40 | pale, mild nephritis | normal |
|  | IB H120 | 6.0 | 16 | pale, mild to moderate nephritis | mucus, tracheitis |
|  | L-1148(p25) | 6.0 | 13 | mild to moderate nephritis | mucus, tracheitis |
|  | L-1148(p50) | 6.0 | 22 | mild to moderate nephritis | tracheitis |
|  | L-1148(p80) | 6.0 | 3 | mild nephritis | normal |
| C | L-1148(p65) | 6.0 | 18 | none | 1x mucus |

*Titer expressed in $^{10}$log $EID_{50}$ per dose

The results show that IB-M41 (virulent strain) had a high cilia score; the maximal score that can be achieved is 40. Strain IB 1449-10 also had a high cilia score. The vaccine strain IB H120 had a low score that complies with regulatory requirements (e.g., less than 25). Passage 8 of strain IB L-1148 had a high score of 39 in study A. There was a strong decrease to 18 at passage level 25. At passage levels 40 and 50 there were increases in ciliastasis score to 31 for p50 in study A. The samples of strain IB L-1148 tested in study A all were contaminated with an ND virus. Passage levels 25 and 50 were tested again after cleaning from ND contamination. This time the ciliastasis scores were clearly lower and within the acceptable range for a vaccine strain. In study B passage 80 was also tested. This passage appeared to give a very low ciliastasis score, much lower than IB H120. It was anticipated that passage level 80 might be attenuated beyond what is necessary for a safe vaccine strain.

Table 7 also shows results of the examinations of the kidneys and the trachea. Mild to moderate nephritis was considered acceptable as long as it was transient. Tracheitis was considered acceptable only if it was transient, the same held for mucus in the trachea. The results show that the passages 8, 25, 40 and 50 of IB L-1148 affected the kidneys, just like the reference vaccine strain IB H120, but not as severe as IB strain 1449-10. Passage 80 also had some effect on the kidneys.

After analyzing the results of Studies A and B, it was decided to produce a batch of IB L-1148 at passage level 65 (i.e., L-1148(p65)) and to assess the safety of the resulting viruses. Passages were prepared from passage 50 to passage 64 by inoculation of eggs each with 0.1 ml of 100-fold dilutions of the pooled supernatants from allantoic fluids from the former passage, until passage level 64. A large batch was produced at passage level 65, under GMP. Eggs were inoculated each with 0.2 ml of a 1000-fold dilution of the allantoic fluid from passage level 64. After 24 hours' incubation at 37° C., the allantoic fluid was harvested in pools. A sample was taken from one of the pools, titrated and subjected to a safety test. The results are summarized in Table 7 (Study C). The results show that the average ciliastasis score was 18, which is similar with what was found in former tests for IB H120. Nephritis was not observed and some mucus was found in the trachea in only one of the 15 chickens.

Conclusion

This Example demonstrates that safe vaccine strains against IB-QX-like viruses can be produced by passaging an IB-QX-like strain in embryonated chicken eggs multiple times. In this Example, passage levels from 25 through 80 resulted in attenuated viruses with safety profiles on par with a known, acceptable IB vaccine.

Example 4

Efficacy of Vaccines Derived from IB-QX-Like Strain L-1148

In this Example, the efficacy of two vaccine strains derived from IB-QX-like strain L-1148 was assessed. The vaccine strains tested were L-1148(p65) and L-1148(p80) (see Example 3).

One day old SPF layer type chickens were vaccinated by spray (0.5 ml per dose). Three weeks after vaccination the chickens were challenged each with a dose of $10^{4.0}$ $EID_{50}$ of IB strain D388 (a virulent IB-QX-like strain isolated in the Netherlands).

The ciliary activity of tracheal explants was examined 5 days after challenge. Immediately after death the trachea was removed, rinsed with and stored in physiologic saline at 37° C. until further processing. Small transverse sections of the trachea were cut by hand. Ciliary activity of 3 sections of the upper part, 4 sections of the middle part and 3 sections of the lower part of the trachea were examined by low-magnification microscopy.

The ciliary activity was scored using the following classification criteria:

| Score | Criteria |
| --- | --- |
| 0 | ≥50% of the tracheal section shows ciliary activity. |
| 1 | <50% of the tracheal section shows ciliary activity. |

For a given tracheal section, ciliary activity was considered as normal when at least 50% (score 0) of the internal ring showed vigorous ciliary movement. A chicken was considered not affected if not fewer than 9 out of 10 rings showed normal ciliary activity. The test was not valid if the tracheal sections were microscopically examined more than 2 hours after sampling of the tracheas.

Results are summarized in Table 8.

TABLE 8

Summary of Efficacy Study

| Vaccine | EID50 per dose | Challenge | N protected/N total |
| --- | --- | --- | --- |
| None | — | No | 19/20 |
| None | — | Yes | 0/20 |
| L-1148(p65) | $10^{3.3}$ | Yes | 20/20 |
| | $10^{3.0}$ | Yes | 20/21 |
| | $10^{2.7}$ | Yes | 20/20 |
| | $10^{2.4}$ | Yes | 0/20 |
| L-1148(p80) | $10^{3.3}$ | Yes | 17/20 |

In the nonvaccinated and nonchallenged control group, one of the 20 chickens showed a decrease in ciliary activity without specified reasons. In the other chickens, cilia movement was normal. In the nonvaccinated challenged group, all chicken showed decreased ciliary activity. In the groups vaccinated with L-1148(p65) and L1148(p80), protection was better than prescribed by regulatory authorities (e.g., at least 80% protected) except in the group vaccinated with $10^{2.4}$ $EID_{50}$ of L-1148(p65) in which no protection was observed.

This Example demonstrates the efficacy of vaccine strains derived from IB-QX-like strains by serial passaging.

Example 5

Safety Assessment of Additional IB-QX-Like Vaccine Strains

Introduction

In this Example, the safety of IB-QX-like strain L-1148 (p80) (also referred to herein as "Master Seed Virus" or "MSV-p80") in chickens was assessed along with strain L-1148 at passage level 101 ("L-1148(p101)") and strain 1449-2 at passage level 18 ("1149-2(p18)")

250 healthy female White Leghorn chicks, divided into five groups of 50 each, were used in this Example in accordance with the study design shown in Table 9.

TABLE 9

Study Design

| Group No. | No. Birds | Vaccine | Age of Vaccination |
| --- | --- | --- | --- |
| 1 | 50 | MSV-p80 | day of hatching |
| 2 | 50 | MSV-p80 | 7 days-old |
| 3 | 50 | L-1148(p101) | day of hatching |
| 4 | 50 | 1449-2(p18) | day of hatching |
| 5 | 50 | Diluent only control | day of hatching |

Vaccination was performed by the oculonasal route, with each chick receiving the corresponding vaccine in a volume of 0.2 mL (0.1 mL in each eye). All vaccines were administered at a dose of $10^{5.0}$ $EID_{50}$/bird.

During the study, birds were observed daily for clinical symptoms. Any clinical sign or mortality was recorded. Birds that died during the study were submitted for post mortem examination.

Oviducts were examined at 11 weeks of age, except for pullets of group 2 which were examined at 12 weeks of age. Pullets were euthanized and the coelomic cavity was opened and the complete oviduct was macroscopically examined externally and internally (opening it longitudinally with a pair of scissors) for the presence of cysts, strictures, deformation or aplasia.

Results

The mortality results are summarized in Table 10.

TABLE 10

Mortality Results

| Group No. | Vaccine | Mortality | Percentage |
|---|---|---|---|
| 1 | MSV-p80 | 2 out of 50 | 4% |
| 2 | MSV-p80 | 1 out of 50 | 2% |
| 3 | L-1148(p101) | 6 out of 50 | 12% |
| 4 | 1449-2(p18) | 11 out of 50 | 22% |
| 5 | Diluent only control | 0 out of 50 | 0% |

The results of oviduct examination are summarized in Table 11.

TABLE 11

Post Mortem Examination of Oviducts

| Group | Vaccine | Age of Vaccination | Cystic-aplasic oviducts | percentage |
|---|---|---|---|---|
| 1 | MSV-p80 | day of hatching | 6 out of 48 | 12.5% |
| 2 | MSV-p80 | 7 days-old | 0 out of 49 | 0% |
| 3 | L-1148(p101) | day of hatching | 4 out of 43 | 9.3% |
| 4 | 1449-2(p18) | day of hatching | 2 out of 39 | 5.1% |
| 5 | Diluent only control | day of hatching | 0 out of 50 | 0% |

In group 1, 6 out of 48 chickens (12.5%) had cystic oviducts and aplasia of the upper segment. One chicken had a small cyst of 4.4 mm in diameter. It was located close in the wall and did not affect the tubular structure of the oviduct.

In group 2, all 49 surviving chickens had a normal ovary and oviduct. One chicken had a small cyst of 2.4×4.1 mm. It was placed close to the ovary but it did not affect the tubular structure of the oviduct.

In group 3, 4 out of 43 (9.3%) chickens had cystic oviducts and aplasia of the upper segment.

In group 4, 2 out of 39 chickens (5.13%) had cystic oviducts and aplasia of the upper segment.

Discussion

The relatively low mortality and low occurrence of cystic-aplasic oviducts observed in birds vaccinated with the test vaccines indicates that these vaccines are generally safe. The MSV-p80 vaccine administered to 7 day old pullets appears to have a particularly good safety profile and complies with the European Pharmacopoeia safety requirements.

Example 6

Reversion to Virulence Study

Introduction

As noted in Example 5, IB-QX-like strain L-1148(p80) was designated Master Seed Virus or "MSV-p80". In this Example, the propensity of MSV-p80 and its back-passaged derivative "MSV+1BP" to revert to virulence was assessed.

The following vaccines were used in this Example:

(A) IB-QX MSV-p80 L-1148(p80)) in a dose of $10^{6.0}$ $EID_{50}$ per chicken.

(B) Back-passaged IB-QX MSV-p80 recovered after 1 chicken back passage ("MSV+1BP") in a dose of $10^{6.0}$ $EID_{50}$ per chicken. The back-passage procedure is as follows: (i) 5 14-day old SPF chickens were vaccinated by eye drop with 0.1 mL containing $10^{4.0}$ $EID_{50}$ per dose of MSV-p80; (ii) The chickens were euthanized four days after vaccination and a suspension of the tracheal mucosa was prepared; (iii) A second group of 5 14-day old SPF chickens was inoculated with the tracheal suspension. The tracheal mucosal samples were tested for the presence of virus by RT-PCR an egg inoculation. At the first chicken back-passage, virus was detected by PCR and by egg inoculation; however, no virus could be detected at the second chicken back-passage. The virus obtained from the tracheal mucosa samples at the first chicken passage was amplified and designated MSV+1BP.

A total of 51 one-day-old SPF chickens were divided into three groups and vaccinated in accordance with the study design shown in Table 12.

TABLE 12

Study Design

| Group | No. Chickens | Vaccine | Dose | Volume |
|---|---|---|---|---|
| 1 | 17 | MSV–p80 | $10^{6.0}$ $EID_{50}$ | 0.1 mL |
| 2 | 17 | MSV+1BP | $10^{6.0}$ $EID_{50}$ | 0.1 mL |
| 3 | 6 | Non-vaccinated controls | — | — |

Vaccination was performed by the oculonasal route, with each chicken receiving the corresponding vaccine in a volume of 0.1 mL (0.05 mL in each eye).

The ciliary activity of tracheal explants was examined on day 5, 7 and 10 after vaccination. Chickens were euthanized by inhalation of 100% $CO_2$. Immediately after death, the trachea was removed and rinsed with and stored in physiologic saline at 37° C. until further processing. Transverse sections of 0.6 mm of the tracheas were made using a McIlwain Tissue Chopper (Mickle Laboratory Engineering Co., Ltd., Surrey, UK). The transverse sections of the tracheas were combined with 2.0 mL physiologic saline at 37° C. in a Petri-dish. Ciliary activity of 3 sections of the upper part, 4 sections of the middle part and 3 sections of the lower part of the tracheas were examined by low-magnification microscopy. All tracheal explants were examined within 2 hours after sampling. The activity of the cilia was scored on a scale of 0 to 4 using the following definitions:

| SCORE | DEFINITION |
|---|---|
| 0 | The cilia in the complete tracheal section showed activity. |
| 1 | The cilia of more than 67% but less than 100% of the tracheal section showed activity. |
| 2 | The cilia of 33% to 67% of the trachea showed activity. |
| 3 | The cilia of less than 33% but more than 0% of the tracheal section showed activity |
| 4 | The cilia in the complete tracheal section showed no activity. |

Chickens in each group were assessed for (a) ciliary activity of tracheal explants, (b) gross pathological examination, (c) histology of the kidneys and (d) serology. Ciliostasis was calculated by dividing the sum of the scores of the tracheal sections that showed cessation by the number of chickens per group. For gross pathological examination, necropsy was performed on each chicken to determine any abnormality that could be related to the vaccine. Histological examination of formalin fixed kidney tissue was performed, and the findings were recorded as: no, mild, moderate or severe nephritis. For serology analysis, serum neutralization and ELISA tests on sera collected from ten one-day-old chickens was performed.
Results
1. Clinical Signs.

No clinical signs attributable to MSV-p80 or MSV+1BP were observed during the study. However, one chicken vaccinated with MSV-p80 was found dead 2 days after vaccination. At necropsy, tracheitis and pneumonia were observed. The cause of death was determined to be suffocation due to a large amount of mucous in the trachea. Infectious Bronchitis is considered to be an unlikely cause of death because none of the other chickens showed any clinical signs and death occurred only after 2 days post-vaccination, a time period that is much less than the incubation period (4 days) for IB.

2. Ciliary Activity.

The ciliostasis scores on days 5, 7 and 10 after vaccination are presented in Table 13. With the exception of 1 tracheal sample of one section, there was no cessation of ciliary activity in any of the tracheal samples collected on day 5 post vaccination. However, on day 7 and 15, a relatively small degree of cessation of ciliary activity was observed in both groups. Average ciliostasis scores were 15 and 10 for MSV-p80 and MSV+1BP, respectively.

3. Pathologic Examination and Histology of the Trachea and Kidneys

Besides some non-specific paleness of the kidneys, no macroscopic abnormalities were observed in tracheas and kidneys. (See Table 13). Some interstitial lymphocellular infiltration was observed during histopathological examination of the kidney samples. The absence of other lesions (granular degeneration, vacuolation and desquamation of tubular epithelium, and absence of massive heterophil infiltration) suggested that the observed lymphocyte infiltration is most likely due to initiation of an immune response.

TABLE 13

Ciliostasis Scores

| Vaccine | Ciliostasis Score days after vaccination | | | | Trachea (macro-scopy) | Kidneys | |
|---|---|---|---|---|---|---|---|
| | 5 | 7 | 10 | Avg. | | Macroscopy | Nephritis |
| MSV + 1BP | 0.0 | 14.8 | 16.4 | 10 | Normal | Normal | None |
| MSV-p80 | 0.2 | 37.4 | 8.4 | 15 | Normal | Normal | None |
| None | 0.0 | 0.0 | 0.2 | 0 | Normal | Normal | None |

4. Serology

No antibodies to Infectious Bronchitis Virus were detected in the pre-sera (data not shown).

Discussion and Conclusions

The average ciliostasis scores for both MSV-p80 and MSV+1BP vaccinated chickens were less than 25, and no chicken showed notable clinical signs of avian infectious bronchitis. It was concluded that MSV-p80 (i.e. L-1148(p80)) is safe for the respiratory tract and kidneys and complies with standard requirements. Furthermore, there is no indication of an increase of virulence of MSV-p80 following back-passage in chickens.

Example 7

Efficacy and Minimal Protective Dose of IB-QX-Like Vaccines

Introduction

In this Example, the minimal protective dose of four different IB-QX-like vaccines was determined in chickens challenged with a virulent IB-QX-like virus.

The following live vaccines were used in this example:

(1) MSV-p80 passaged an additional two times, referred to herein as "MSV-p80 X+2" (which therefore has been passaged a total of 82 times);

(2) MSV-p80 passaged an additional five times, referred to herein as "MSV-p80 X+5" (which has been passaged a total of 85 times);

(3) Strain L-1148 passaged 101 times, referred to herein as L-1148(p101); and (4) Strain 1449-2 passaged 19 times, referred to herein as 1449-2(p19).

A total of 208 healthy one-day-old SPF-chickens was used in this study. Chickens were vaccinated with different doses of the aforementioned vaccines by coarse spray (using a commercially available flower sprayer). 21 days after vaccination the chickens were challenged with $10^{4.0}$ $EID_{50}$ of virulent IB-QX-like strain D388 by eye drop (0.05 mL in each eye). Five days after challenge the ciliary activity in tracheal explants was determined in 20 chickens. Blood was taken on the day of vaccination and on 21 days after vaccination. The experimental design is summarized in Table 14.

TABLE 14

Study Design

| Group | Vaccine | Amount per dose | No. | Events (day of life) | | |
|---|---|---|---|---|---|---|
| | | | | 1 | 21 | 26 |
| 1 | MSV-p80 X + 2 | $10^{3.0}$ $EID_{50}$ | 22 | Vaccination & Serology | Challenge (n = 20) & Serology | CST & Sampling of kidneys and tracheas |
| 2 | MSV-p80 X + 5 | $10^{2.7}$ $EID_{50}$ | 22 | | | |
| 3 | MSV-p80 X + 5 | $10^{3.0}$ $EID_{50}$ | 22 | | | |
| 4 | MSV-p80 X + 5 | $10^{3.3}$ $EID_{50}$ | 22 | | | |
| 5 | MSV-p80 X + 2 | $10^{3.3}$ $EID_{50}$ | 22 | | | |
| 6 | 1449-2(p19) | $10^{3.3}$ $EID_{50}$ | 22 | | | |
| 7 | L-1148(p101) | $10^{3.3}$ $EID_{50}$ | 22 | | | |
| 8 | unvaccinated/ challenged | N/A | 22 | Serology | | |
| 9 | unvaccinated/ unchallenged | N/A | 22 | Serology | Serology | |

The ciliary activity of the tracheal explants was examined in 20 chickens 5 days after challenge. Chickens were euthanized and immediately after death the trachea was removed, rinsed with and stored in physiologic saline at 37° C. until further processing. Small transverse sections of the trachea were cut by hand. Ciliary activity of three sections of the upper part, four sections of the middle part, and three sections of the lower part of the trachea were examined by low-magnification microscopy. The ciliary activity was scored using the following classification criteria:

| SCORE | CRITERIA |
|---|---|
| 0 | At least 50% of the tracheal section showed ciliary activity. |
| 1 | Less than 50% of the tracheal section showed ciliary activity. |

For a given tracheal section, ciliary activity was considered normal when at least 50% (score 0) of the internal ring showed vigorous ciliary movement. A chicken was considered not affected if not fewer than 9 out of 10 rings showed normal ciliary activity. The test was not deemed valid if the tracheal sections were microscopically examined more than 2 hours after sampling of the tracheas.

Necropsy was performed on each chicken at 5 days after challenge to determine any abnormality in the kidneys that could be a result of the IBV infection. The following criteria were used to score the macroscopic findings in the kidneys: normal=n.a.; swollen, pale or urate crystals=1.

Results

1. Clinical Signs Following Vaccination

The ciliary and gross pathological examination results are summarized in Table 15.

TABLE 15

Cilia movement Test Results and Other Observations

| group | Vaccine | Amount per dose | Protected/ Total (%) | Other observations Kidneys | Trachea |
|---|---|---|---|---|---|
| 1 | MSV-p80 X + 2 | $10^{3.0}$ $EID_{50}$ | 18/19 (95) | none | none |
| 2 | MSV-p80 X + 5 | $10^{2.7}$ $EID_{50}$ | 0/20 (0) | none | none |
| 3 | MSV-p80 X + 5 | $10^{3.0}$ $EID_{50}$ | 17/20 (85) | none | none |
| 4 | MSV-p80 X + 5 | $10^{3.3}$ $EID_{50}$ | 17/20 (85) | none | none |
| 5 | MSV-p80 X + 2 | $10^{3.3}$ $EID_{50}$ | 18/20 (90) | none | none |
| 6 | 1449-2(p19) | $10^{3.3}$ $EID_{50}$ | 20/20 (100) | 1/20* | none |
| 7 | L-1148(p101) | $10^{3.3}$ $EID_{50}$ | 13/20 (65) | none | none |
| 8 | unvaccinated/ challenged | N/A | 0/20 (0) | none | none |
| 9 | unvaccinated/ unchallenged | N/A | 20/20 (100) | none | none |

*One of the chickens had kidney lesions.

The results shown in Table 15 show that the MSV-p80 vaccine is efficacious as long as a dose of $10^{3.0}$ $EID_{50}$ or more is used. A dose of $10^{2.7}$ $EID_{50}$ did not induce protection. There was a small, non-significant difference in protection generated by MSV-p80 X+2 and MSV-p80 X+5; X+2 gave somewhat better protection than X+5 in this study. Strain L-1148 (p101) gave less protection than the lower passage levels.

Summary

This Example further demonstrates the safety and efficacy of vaccines derived from the IB-QX MSV-p80.

Example 8

Spread of Attenuated IB QX Between Chickens and Dissemination in the Body

Introduction

This Example investigated the dissemination of attenuated IB QX vaccine strain IB-QX MSV-p80 in the body and the spreading of IB-QX MSV-p80 to non-vaccinated chickens.

Experimental Design

1. Animals

A total of 165 SPF-chickens were divided into the groups shown in Table 16. Chickens were housed according to normal procedures. Food and water was available ad lib. All chickens were observed for clinical signs throughout the study.

TABLE 16

Animals

| Group | Age (n) | Description |
|---|---|---|
| 1 | 1 day (55) | Vaccinated with $10^{5.0}$ $EID_{50}$ IB-QX MSV-p80 per chicken. 30 chickens added to group 2 chickens three days following vaccination. |
| 2 | 7 days (35) | Non-vaccinated chickens. |
| 3 | 14 days (35) | Non-vaccinated chickens (added to group 2 at 14 days following vaccination of group 1). |
| 4 | 1 day (30) | Non-vaccinated chickens (added to group 2 at 7 days following vaccination of group 1). |
| 5 | 1 day (10) | Used for collection of blood |

2. Methods 2.1 Vaccination

One vial of IB-QX MSV-p80 containing $10^{8.2}$ $EID_{50}$ was diluted in 157.5 ml buffer and used within 2 h of preparation. Group 1 one day old chickens were vaccinated with 0.1 ml of diluted virus by eye-drop ($10^{5.0}$ $EID_{50}$ IB-QX MSV-p80 per chicken). After vaccination, samples of used vaccines were stored at −50° C. Back titration was performed to determine the titer of virus in the administered vaccine. Administered vaccine was found to contain $10^{6.07}$ $EID_{50}$ IB QX per ml, corresponding to a dose of $10^{5.07}$ $EID_{50}$ per chicken.

2.2 Experimental Design

Group 1 chickens were vaccinated with IB-QX MSV-p80. Three days after vaccination, 30 vaccinated chickens from group 1 were added to a containment unit containing 35 non-vaccinated chickens from group 2 from the same age and origin. Seven days after vaccination, a group of 30 non-vaccinated chickens from group 4 were added to the containment unit. At 14 days following vaccination, 35 non-vaccinated chickens from group 3 of the same age and origin as the vaccinated chickens were added to the containment unit. At regular intervals, 2 chickens from each of groups 2-4 were killed by inhalation of 100% $CO_2$ and samples were taken from bursa, duodenum, lung, kidney, pancreas and trachea to determine the presence of IBV.

IBV was detected in organ samples by immunohistochemical staining for IBV epitope 48.4 (a nucleoprotein) of formalin fixed samples. After chicken was killed, a swab was taken from the cloaca and oropharynx.

The presence of IB QX in the swabs was detected by PCR using SuperScript™ III one step qRT-PCR kit from Invitrogen. PCR mixtures contained 25 µl 2× mix, 18 µl water, 1 µl Taq platinum, 2 µl forward primer, 2 µl reverse primer and 2 µl template (RNA). The following primers were used:

```
IBV Common Primers
SX3 + A/B forward
5'-TAATACTGGYAATTTTTCAGATGG-3'   (SEQ ID NO: 5)

SX4-reverse
5'-AATACAGATTGCTTACACCACC-3'    (SEQ ID NO: 6)
```

-continued

```
IB QX Specific Primers
Alg-QX-139 forward
5'-GCTTATGCAGTAGTCAAT-3'         (SEQ ID NO: 7)

Alg-QX-394-reverse
5'-CACGTGGAATCATGCCTGTTAT-3'     (SEQ ID NO: 8)
```

Trachea RNA was used as template. Virus was used as positive control.

RT-PCR was performed according to the following program:

1. 30 min 50° C.
2. 10 min 95° C.
3. 30 sec 95° C.
4. 30 sec 50° C.
5. 45 sec 72° C., steps 3-5 for 40 cycles
6. 7 min 72° C.
7. 5 min 4° C.

RT-PCR products were analyzed by agarose gel electrophoresis.

Blood samples were taken from 10 1-day-old chickens and on day 21 of the study from 10 chickens of each of groups 1, 2, 3 and 4. Blood was collected by decapitation of the 1-day-old chickens or by puncture of the wing vein. Antibody titers were determined with the Flockchek™ IBV antibody test kit available from IDEXX, US or the Flockscreen™ IB-HI kit from X-Ovo, France.

3. Results

Results are summarized in Table 17.

| Group | Method | Organ | Days After Vaccination | | | | | | | | | |
|---|---|---|---|---|---|---|---|---|---|---|---|---|
| | | | 2 | 4 | 7 | 9 | 11 | 14 | 16 | 18 | 21 | 23 |
| 1 | Immuno-histology | Bursa | − | − | − | − | − | − | − | | | |
| | | Duodenum | − | − | − | − | − | − | − | | | |
| | | Lung | − | − | − | − | − | − | − | | | |
| | | Kidney | − | − | − | − | − | − | − | | | |
| | | Pancreas | − | + | − | − | − | − | − | | | |
| | | Trachea | − | + | + | + | + | − | − | | | |
| | PCR | Cloaca swab | − | − | − | − | − | + | − | − | − | − |
| | | Larynx swab | + | + | + | − | + | − | − | − | − | − |

| Group | Method | Organ | Days After First Contact With Vaccinated Chickens | | | | | | | | |
|---|---|---|---|---|---|---|---|---|---|---|---|
| | | | 1 | 4 | 6 | 8 | 11 | 13 | 15 | 18 | 20 |
| 2 | Immuno-histology | Bursa | − | − | − | − | − | − | − | | |
| | | Duodenum | − | − | − | − | − | − | − | | |
| | | Lung | − | − | − | − | − | − | − | | |
| | | Kidney | − | − | − | − | − | − | − | | |
| | | Pancreas | − | − | − | − | + | − | − | | |
| | | Trachea | − | − | − | + | − | − | − | | |
| | PCR | Cloaca swab | − | − | − | − | + | − | + | − | − |
| | | Larynx swab | − | + | + | − | − | − | + | − | − |

| Group | Method | Organ | Days After First Contact With Vaccinated Chickens | | | | | |
|---|---|---|---|---|---|---|---|---|
| | | | 2 | 4 | 7 | 9 | 11 | 14 |
| 3 | Immuno-histology | Bursa | − | | | | | |
| | | Duodenum | − | | | | | |
| | | Lung | − | | | | | |
| | | Kidney | − | | | | | |
| | | Pancreas | − | | | | | |
| | | Trachea | − | | | | | |
| | PCR | Cloaca swab | − | − | − | − | − | − |
| | | Larynx swab | − | + | + | − | + | + |
| 4 | Immuno-histology | Bursa | − | − | − | − | | |
| | | Duodenum | − | − | − | − | | |
| | | Lung | − | − | − | − | | |
| | | Kidney | − | − | − | − | | |
| | | Pancreas | − | − | − | − | | |
| | | Trachea | − | − | − | + | | |
| | PCR | Cloaca swab | + | − | − | − | − | − |
| | | Larynx swab | − | − | − | + | − | + |

No respiratory signs or other clinical signs indicating IB were observed during the study. One chicken in group 2 died due to inflammation of the yolk sac. One chicken in group 1 died due to cannibalism. For serological tests, hemagglutination inhibition (HI) tests were performed with the IB 793B antigen because IB QX antigen did not give good hemagglutination. No IB antibodies were detected in any sera by the HI-test or by ELISA.

IHT-staining detected IB QX in the tracheas of chickens from 4-11 days and in the pancreas on day 4 and day 11 after first exposure to virus. IHT-staining did not detect IB QX in the bursa, duodenum, lungs or kidneys.

The presence of IB QX was detected by IHT-staining and PCR of laryngeal and cloacal swabs from all groups. IB was detected by PCR in cloacal and laryngeal swabs from 2-15 days after first-exposure to IB QX. Laryngeal swabs were positive for IB QX more frequently than cloacal swabs.

4. Discussion 4.1 Dissemination

Detection of IB QX in the trachea was expected, because the upper respiratory tract is the main site of IBV replication. Subsequently viremia occurs and the virus disseminates to other tissues. This was demonstrated by detection of IB QX in the pancreas. Although IBV is primarily an epitheliotropic virus, IB QX at passage level 80 could not be detected in the kidneys or lungs, suggesting that virus was cleared from these organs at the administered vaccine dose of $10^{5.0}$ $EID_{50}$ per chicken. In safety studies of with IB QX at the same passage level in which chickens were vaccinated with $10^{6.0}$ $EID_{50}$ IB QX per chicken, virus was detected in the kidney and lungs for 10 days after vaccination. In the present study, IB QX was detected in the trachea for 11 days and the larynx for 15 days. Reports in the literature found IB could be detected in the trachea for 5-10 days after infection during the clinical phase and for up to 28 days after infection in the trachea. Although IB QX was detected in the pancreas, no abnormality was observed during gross pathological examination.

4.2 Spreading

Spreading of IB QX was clearly demonstrated as the presence of IB QX was detected in all of the non-vaccinated groups.

4.3 Safety

IB QX at passage level 80 administered at a dose of $10^{5.07}$ $EID_{50}$ per chicken by eye drop did not cause any vaccine-related clinical signs after vaccination. No clinical signs of IB were observed in non-vaccinated chickens that were infected with IB QX following exposure to vaccinated chickens.

5. Conclusions

Following vaccination, multiplication of the IB-QX MSV-p80 virus occurred in the trachea and IB QX disseminated to other organs. IB-QX MSV-p80 spread between chickens at least once. IB-QX MSV-p80 and the vaccine that passaged between the groups was safe.

Example 9

Combined Vaccination with IB MM and IB QX Vaccines

The efficacy of combined vaccination with IB MM and IB QX vaccines was tested in SPF chickens. Chickens were vaccinated with Poulvac IBMM vaccine (Fort Dodge Animal Health) on day 0 and at day 14 with live IB QX vaccine. Vaccinated strains were challenged with IB strain IT02 at day 14 and with IB strain 793B at day 35. Results of vaccination were determined by analysis of ciliostasis tests (CST) of tracheal sections and determination of kidney pathology. Vaccinated chickens were completely protected from challenge with strains IT02 and 793.

A summary of the respective vaccination protocol and results is given in Table 18.

TABLE 18

| | Vaccination | | | |
|---|---|---|---|---|
| | Day 1 | Day 14 | Challenge | CST | Kidney Lesions |
| 1 | IB MM | IB QX | IB 793B | 0 | 0.8 |
| 2 | IB MM | IB QX | IB IT 02 | 0 | 0.0 |
| 3 | IB Primer | IB QX | IB 793B | 0 | 0.0 |
| 4 | None | None | IB IT 02 | 19.8 | 0.0 |
| 5 | None | None | IB 793B | 29.4 | 0.8 |
| 6 | None | None | None | 0 | 0.0 |
| 7 | IB Primer + IB QX | None | IB 793B | 2.5 | 0.8 |
| 8 | None | None | IB 793B | 0 | 1.2 |
| 9 | None | None | None | 0 | 0.0 |

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. An isolated attenuated infectious bronchitis (IB) virus deposited with the ECACC under provisional accession No. 09061004.

2. A vaccine comprising the isolated attenuated infectious bronchitis (IB) virus of claim 1 further comprising a pharmaceutically acceptable carrier.

3. A method for vaccinating a chicken against infectious bronchitis (IB), said method comprising administering the vaccine composition of claim 1 to said chicken.

4. The method of claim 3 further comprising vaccinating against one or more additional infectious agents other than an IB virus.

* * * * *